United States Patent [19]
Tung et al.

[11] Patent Number: 5,691,372
[45] Date of Patent: Nov. 25, 1997

[54] OXYGENATED-HETEROCYCLE CONTAINING SULFONAMIDE INHIBITORS OF ASPARTYL PROTEASE

[75] Inventors: Roger D. Tung, Arlington; Govinda Rao Bhisetti, Lexington, both of Mass.

[73] Assignee: Vertex Pharmaceuticals Incorporated, Cambridge, Mass.

[21] Appl. No.: 424,810

[22] Filed: Apr. 19, 1995

[51] Int. Cl.$^6$ ............... A61K 31/335; A61K 31/34; A61K 31/35; C07D 319/06
[52] U.S. Cl. ............... 514/452; 549/371; 549/372; 549/373; 549/396; 549/419; 549/449; 549/475; 514/467; 514/456; 514/460; 514/473
[58] Field of Search ............... 549/371, 372, 549/373; 514/452

[56] References Cited

U.S. PATENT DOCUMENTS

| | | | |
|---|---|---|---|
| 3,743,722 | 7/1973 | Mohrs et al. | 424/98 |
| 4,330,542 | 5/1982 | Descamps et al. | 424/248.5 |
| 4,629,724 | 12/1986 | Ryono et al. | 514/18 |
| 5,196,438 | 3/1993 | Martin et al. | 514/311 |
| 5,354,866 | 10/1994 | Kempf et al. | 546/265 |

FOREIGN PATENT DOCUMENTS

| | | | |
|---|---|---|---|
| 0 022 118 | 1/1981 | European Pat. Off. | C07C 143/822 |
| 0 181 071 | 3/1986 | European Pat. Off. | C07K 5/06 |
| 0 264 795 | 4/1988 | European Pat. Off. | C07K 5/00 |
| 0 346 847 | 12/1989 | European Pat. Off. | C07D 207/16 |
| 0 364 804 | 4/1990 | European Pat. Off. | C07D 211/30 |
| 0 468 641 | 1/1992 | European Pat. Off. | C07K 5/02 |
| 0 486 948 | 5/1992 | European Pat. Off. | C07D 213/26 |
| 0 541 168 | 5/1993 | European Pat. Off. | C07D 217/26 |
| 3542567 | 6/1986 | Germany | C07K 5/06 |
| 59-048449 | 3/1984 | Japan | C07C 103/375 |
| 61-071830 | 4/1986 | Japan | B01F 17/46 |
| 2167759 | 6/1986 | United Kingdom | C07K 5/06 |
| 2200115 | 7/1988 | United Kingdom | C07C 103/00 |
| WO 90/07329 | 7/1990 | WIPO | A61K 31/19 |
| WO 91/00725 | 1/1991 | WIPO | . |
| WO 91/18866 | 12/1991 | WIPO | C07C 237/22 |
| WO 92/08688 | 5/1992 | WIPO | C07D 215/48 |
| WO 92/08698 | 5/1992 | WIPO | C07D 215/48 |
| WO 92/08699 | 5/1992 | WIPO | C07D 215/48 |
| WO 92/08700 | 5/1992 | WIPO | C07D 215/48 |
| WO 92/08701 | 5/1992 | WIPO | C07D 215/48 |
| WO 92/17176 | 10/1992 | WIPO | A61K 31/44 |
| WO 93/23368 | 11/1993 | WIPO | C07C 275/24 |
| WO 93/23379 | 11/1993 | WIPO | C07D 217/26 |
| WO 93/23388 | 11/1993 | WIPO | C07D 303/36 |
| WO 94/04491 | 3/1994 | WIPO | C07K 13/00 |
| WO 94/04492 | 3/1994 | WIPO | C07C 311/29 |
| WO 94/04493 | 3/1994 | WIPO | C07C 317/44 |
| WO 94/10134 | 5/1994 | WIPO | C07C 307/06 |
| WO 94/10136 | 5/1994 | WIPO | C07C 317/44 |
| WO 94/18192 | 8/1994 | WIPO | C07D 401/14 |
| WO 94/19322 | 9/1994 | WIPO | C07D 209/34 |

OTHER PUBLICATIONS

R.D. Bindal et al., "Ab Initio Calculations on N-Methylmethanesulfonamide and Methyl Methanesulfonate for the Development of Force Field Torsional Parameters and Their Use in the Conformational Analysis of Some Novel Estrogens", *J. Am. Chem. Soc.*, 112, pp. 7861–7868 (1990).

R. Bone et al., "X–ray Crystal Structure of the HIV Protease Complex with L–700, 417, and Inhibitor with Pseudo $C_2$ Symmetry", *J. Am. Chem. Soc.*, 113, pp. 9382–9384 (1991).

R.F. Borch et al., "The Cyanohybridoborate Anion as a Selective Reducing Agent", *J. Am. Chem. Soc.*, 93, pp. 2897–2904 (1971).

J.C. Craig et al., "Antiviral Synergy Between Inhibitors of HIV Proteinase and Reverse Transcriptase", *Antiviral Chem. and Chemotherapy*, 4(3), pp. 161–166 (1990).

S. Crawford et al., "A Deletion Mutation in the 5' Part of the pol Gene of Moloney Murine Leukemia Virus Blocks Proteolytic Processing of the gag and pol Polyproteins", *J. Virol.*, 53, pp. 899–907 (1985).

M. Cushman et al., "Development of Methodology for the Synthesis of Stereochemically Pure Phe$\psi$ [CH$_2$N] Pro Linkages in HIV Protease Inhibitors", *J. Org. Chem.*, 56, pp. 4161–4167 (1991).

D.S. Dhanoa et al., "The Synthesis of Potent Macrocyclic Renin Inhibitors", *Tetrahedron Lett.*, 33, pp. 1725–1728 (1992).

G.B. Dreyer et al., "Hydroxyethylene Isostere Inhibitors of Human Immunodeficiency Virus–1 Protease: Structure–Activity Analysis Using Enzyme Kinetics, X–ray Crystallography, and Infected T–Cell Assays", *Biochemistry*, 31, pp. 6646–6659 (1992).

B.E. Evans et al., "A Stereocontrolled Synthesis of Hydroxyethylene Dipeptide Isosteres Using Novel, Chiral Aminoalkyl Epoxides and γ–(Aminoalkyl) γ–Lactones", *J. Org. Chem.*, 50, pp. 4615–4625 (1985).

G.A. Flynn et al., "An Acyl–Iminium Ion Cyclization Route to a Novel Conformationally Restricted Dipeptide Mimic: Applications to Angiotensin–Converting Enzyme Inhibition", *J. Am. Chem. Soc.*, 109, pp. 7914–7915 (1989).

G. Fontenot et al., "PCR Amplification of HIV–1 Proteinase Sequences Directly from Lab Isolates Allows Determination of Five Conserved Domains", *Virology*, 190, pp. 1–10 (1992).

P.G. Gassman and T.L. Guggenheim, "Opening of Epoxides with Trimethylsilyl Cyanide to Produce β–Amino Alcohols", *J. Am. Chem. Soc.*, 104, pp. 5849–5850 (1982).

(List continued on next page.)

*Primary Examiner*—Jose' G. Dees
*Assistant Examiner*—Laura L. Stockton
*Attorney, Agent, or Firm*—Fish & Neave; James F. Haley, Jr.; Andrew S. Marks

[57] ABSTRACT

The present invention relates to a novel class of sulfonamides which are aspartyl protease inhibitors. This invention also relates to pharmaceutical compositions comprising these compounds. The compounds and pharmaceutical compositions of this invention are particularly well suited for inhibiting HIV–1 and HIV–2 protease activity and consequently, may be advantageously used as anti-viral agents against the HIV–1 and HIV–2 viruses. This invention also relates to methods for inhibiting the activity of HIV aspartyl protease using the compounds of this invention.

46 Claims, No Drawings

OTHER PUBLICATIONS

E.E. Gilbert, "Recent Developments in Preparative Sulfonation and Sulfation", *Synthesis*, 1969, pp. 3–10 (1969).

A. Goldblum, "Modulation of the Affinity of Aspartic Proteases by the Mutated Residues in Active Site Models", *FEBS*, 261, pp. 241–244 (1990).

D. Grobelny et al., "Selective Phosphinate Transition–State Analogue Inhibitors of the Protease of Human Immunodeficiency Virus", *Biochem. Biophys. Res. Commun.*, 169, pp. 1111–1116 (1990).

G.D. Hartman et al., "4–Substituted Thiophene–and Furan–2–sulfonamides as Topical Carbonic Anhydrase Inhibitors", *J. Med. Chem.*, 35, pp. 3822–3831 (1992).

J.R. Huff, "HIV Protease: A Novel Chemotherapeutic Target for AIDS", *Journal of Medicinal Chemistry*, 34(8), pp. 2305–2314 (1991).

K.Y. Hui et al., "A Rational Approach in the Search for Potent Inhibitors Against HIV Proteinase", *FASEB*, 5, pp. 2606–2610 (1991).

N.E. Kohl et al., "Active HIV Protease Is Required for Viral Infectivity", *Proc. Natl. Acad. Sci. USA*, 85, pp. 4686–4690 (1988).

X. Lin et al., "Enzymic Activities of Two–Chain Pepsinogen, Two–Chain Pepsin, and the Amino–Terminal Lobe of Pepsinogen", *J. Biol. Chem.*, 267(24), pp. 17257–17263 (1992).

K.P. Manfredi et al., "Examination of HIV–1 Protease Secondary Structure Specificity Using Conformationally Constrained Inhibitors", *J. Med. Chem.*, 34, pp. 3395–3399 (1991).

F.R. Marshall, "Computer–Aided Drug Design", *Ann. Ref. Pharmacol. Toxicol.*, 27. pp. 193–213 (1987).

J.A. Martin, "Recent Advances in the Design of HIV Proteinase Inhibitors", *Antiviral Research*, 17, pp. 265–278 (1992).

T.D. Meek et al., "Inhibition of HIV–1 Protease in Infected T–Lymphocytes by Synthetic Peptide Analogues", *Nature*, 343, pp. 90–92 (1990).

M. Miller et al., "Structure of Complex of Synthetic HIV–1 Protease with a Substrate–Based Inhibitor at 2.3 Å Resolution", *Science*, 246, pp. 1149–1152 (1989).

M. Miller et al., "Crystal Structure of a Retroviral Protease Proves Relationship to Aspartic Protease Family", *Nature*, 337, pp. 576–579 (1989).

H. Mitsuya and S. Broder, "Inhibition of the in vitro infectivity and Cytopathic Effect of Human T–Lymphotropic Virus Type III/Lymphoadenopathy–Associated Virus (HTLV–III/LAV) by 2',3'–Dideoxynucleosides", *Proc. Natl. Acad. Sci. USA*, 83, pp. 1911–1915 (1986).

K.H.M. Murthy et al., "Crystal Structures at 2.2–Å Resolution of Hydroxyethylene–Based Inhibitors Bound to Human Immunodeficiency Virus Type 1 Protease Show That the Inhibitors Are Present in Two Distinct Orientations", *J. Biol. Chem.*, 267, pp. 22770–22778 (1992).

J.B. Nichols et al., "A Molecular Mechanics Valence Force Field for Sulfonamides Derived by ab initio Methods", *J. Phys. Chem.*, 95, pp. 9803–9811 (1991).

L.E. Overman and L.A. Flippin, "Facile Aminolysis of Epoxides with Diethylaluminum Amides", *Tetrahedron Letters*, 195, pp. 195–198 (1981).

J. Palca, "Shooting at a New HIV Target", *Science*, 247, p. 410 (1990).

L.H. Pearl et al., "A Structural Model for the Retroviral Proteases", *Nature*, 329. pp. 329–351 (1987).

M. Popvic et al., "Detection, Isolation, and Continuous Production of Cytopathic Retroviruses (HTLV–III) from Patients with AIDS and Pre–AIDs", *Science*, 224, pp. 497–500 (1984).

G.H. Posner and D.Z. Rogers, "Organic Reactions at Alumina Surfaces. Mild and Selective Opening of Epoxides by Alcohols, Thiols, Benzeneselenol, Amines, and Acetic Acid", *J. Am. Chem. Soc.*, 99, 8208–8218 (1977).

M.D. Power et al., "Nucleotide Sequence of SRV–1, a Type D Simian Acquired Immune Deficiency Syndrome Retrovirus" *Science*, 231, pp. 1567–1573 (1986).

N.A. Roberts, "Rational Design of Peptide–Based HIV Proteinase Inhibitors", *Science*, 248, pp. 358–361 (1990).

S. Scharpe et al., "Proteases and Their Inhibitors: Today and Tomorrow", *Biochimie*, 73, pp. 121–126 (1991).

S.K. Sharma et al., "Could Angiotensin I Be Produced from a Renin Substrate by the HIV–1 Protease?", *Anal. Biochem.*, 198, pp. 363–367 (1991).

H. Toh et al., "Close Structural Resemblance Between Putative Polymerase of a Drosophila Transposable Genetic Element 17.6 and pol Gene Product of Moloney Murine Leukemia Virus", *EMBO J.*, 4. pp. 1267–1272 (1985).

OXYGENATED-HETEROCYCLE CONTAINING SULFONAMIDE INHIBITORS OF ASPARTYL PROTEASE

TECHNICAL FIELD OF THE INVENTION

The present invention relates to a novel class of sulfonamides which are aspartyl protease inhibitors. In one embodiment, this invention relates to a novel class of HIV aspartyl protease inhibitors characterized by specific structural and physicochemical features. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting the activity of HIV aspartyl protease using the compounds of this invention.

BACKGROUND OF THE INVENTION

The human immunodeficiency virus ("HIV") is the causative agent for acquired immunodeficiency syndrome ("AIDS")—a disease characterized by the destruction of the immune system, particularly of $CD4^+$ T-cells, with attendant susceptibility to opportunistic infections—and its precursor AIDS-related complex ("ARC")—a syndrome characterized by symptoms such as persistent generalized lymphadenopathy, fever and weight loss.

As in the case of several other retroviruses, HIV encodes the production of a protease which carries out post-translational cleavage of precursor polypeptides in a process necessary for the formation of infectious virions (S. Crawford et al., "A Deletion Mutation in the 5' Part of the pol Gene of Moloney Murine Leukemia Virus Blocks Proteolytic Processing of the gag and pol Polyproteins", *J. Virol.*, 53, p. 899 (1985)). These gene products include pol, which encodes the virion RNA-dependent DNA polymerase (reverse transcriptase), an endonuclease, HIV protease, and gag, which encodes the core-proteins of the virion (H. Toh et al., "Close Structural Resemblance Between Putative Polymerase of a Drosophila Transposable Genetic Element 17.6 and pol gene product of Moloney Murine Leukemia Virus", *EMBO J.*, 4, p. 1267 (1985); L. H. Pearl et al., "A Structural Model for the Retroviral Proteases", Nature., pp. 329–351 (1987); M. D. Power et al., "Nucleotide Sequence of SRV-1, a Type D Simian Acquired Immune Deficiency Syndrome Retrovirus", *Science*, 231, p. 1567 (1986)).

A number of synthetic anti-viral agents have been designed to target various stages in the replication cycle of HIV. These agents include compounds which block viral binding to $CD4^+$ T-lymphocytes (for example, soluble CD4), and compounds which interfere with viral replication by inhibiting viral reverse transcriptase (for example, didanosine and zidovudine (AZT)) and inhibit integration of viral DNA into cellular DNA (M. S. Hirsh and R. T. D'Aquila, "Therapy for Human Immunodeficiency Virus Infection", *N.Eng.J.Med.*, 328, p. 1686 (1993)). However, such agents, which are directed primarily to early stages of viral replication, do not prevent the production of infectious virions in chronically infected cells. Furthermore, administration of some of these agents in effective amounts has led to cell-toxicity and unwanted side effects, such as anemia and bone marrow suppression.

More recently, drug design efforts have been directed toward creating compounds which inhibit the formation of infectious virions by interfering with the processing of viral polyprotein precursors. Processing of these precursor proteins requires the action of virus-encoded proteases which are essential for replication (Kohl, N. E. et al. "Active HIV Protease is Required for Viral Infectivity" *Proc. Natl. Acad. Sci. USA*, 85, p. 4686 (1988)). The anti-viral potential of HIV protease inhibition has been demonstrated using peptidal inhibitors. Such peptidal compounds, however, are typically large and complex molecules that tend to exhibit poor bioavailability and are not generally consistent with oral administration. Accordingly, the need still exists for compounds that can effectively inhibit the action of viral proteases, for use as agents for preventing and treating chronic and acute viral infections. Such agents would be expected to act as effective therapeutic agents in their own right. In addition, since they act at a separate stage in the virus life cycle from previously described antiretroviral agents, the administration of a combination of agents would be expected to result in increased therapeutic efficacy.

SUMMARY OF THE INVENTION

The present invention provides a novel class of compounds, and pharmaceutically acceptable derivatives thereof, that are useful as inhibitors of aspartyl proteases, in particular, HIV aspartyl protease. These compounds can be used alone or in combination with other therapeutic or prophylactic agents, such as anti-virals, antibiotics, immunomodulators or vaccines, for the treatment or prophylaxis of viral infection.

According to a preferred embodiment, the compounds of this invention are capable of inhibiting HIV viral replication in human $CD_4^+$ cells including T-cells, monocytic lines including macrophages and dendrocytes and other permissive cells. These compounds are useful as therapeutic and prophylactic agents to treat or prevent infection by HIV-1 and related viruses which may result in asymptomatic infection, AIDS-related complex ("ARC"), acquired immunodeficiency syndrome ("AIDS"), or similar disease of the immune system.

It is a principal object of this invention to provide a novel class of sulfonamides which are aspartyl protease inhibitors, and particularly, HIV aspartyl protease inhibitors. This novel class of sulfonamides is represented by formula I:

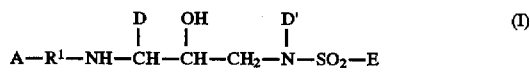

wherein:
  each $R^1$ is independently selected from the group consisting of —C(O)—, —S(O)$_2$—, —C(O)—C(O)—, —O—C(O)—, —O—S(O)$_2$, —NR$^2$—S(O)$_2$—, —NR$^2$—C(O)— and —NR$^2$—C(O)—C(O)—;

each A is independently selected from the group consisting of 5–7 membered non-aromatic monocyclic oxygenated heterocycles containing from 1–3 endocyclic oxygens, which may be optionally benzofused, optionally attached through a $C_1$–$C_3$ alkyl linker and optionally fused with a 5–7 membered monocyclic heterocycle containing from 1–2 endocyclic heteroatoms, and wherein tetrahydrofuran and tetrahydrofurotetrahydrofuran are expressly excluded;

each Ht is independently selected from the group consisting of $C_3$–$C_7$ carbocycle; $C_6$–$C_{10}$ aryl; phenyl fused with heterocycle; and heterocycle; wherein any member of said Ht may be optionally substituted with one or more substituents selected from the group consisting of oxo, —OR$^2$, —R$^2$, —N(R$^2$)(R$^2$), —NHOH, —R$^2$—

OH, —CN, —CO$_2$R$^2$, —C(O)—N(R$^2$)(R$^2$), —S(O)$_2$—N(R$^2$)(R$^2$), —N(R$^2$)—C(O)—R$^2$, —C(O)—R$^2$, —S(O)$_n$—R$^2$, —OCF$_3$, —S(O)$_n$—R$^6$, —N(R$^2$)—S(O)$_2$ (R$^2$), halo, —CF$_3$, —NO$_2$, —R$^6$ and —O—R$^6$;

each R$^2$ is independently selected from the group consisting of H and C$_1$–C$_3$ alkyl optionally substituted with R$^6$;

each R$^3$ is independently selected from the group consisting of H, Ht, C$_1$–C$_6$ alkyl and C$_2$–C$_6$ alkenyl wherein any member of said R$^3$, except H, may be optionally substituted with one or more substituents selected from the group consisting of —OR$^2$, —C(O)—NH—R$^2$, —S(O)$_n$—N(R$^2$)(R$^2$), Ht, —CN, —SR$^2$, —CO$_2$R$^2$, NR$^2$—C(O)—R$^2$;

each n is independently 1 or 2;

each D and D' is independently selected from the group consisting of R$^6$; C$_1$–C$_5$ alkyl, which may be optionally substituted with one or more groups selected from —OR$^2$, —R$^3$, —S—R$^6$—O—R$^6$ and R$^6$; C$_2$–C$_4$ alkenyl, which may be optionally substituted with one or more groups selected from the group consisting of —OR$^2$, —R$^3$, —O—R$^6$ and R$^6$; and C$_1$–C$_6$ carbocycle, which may be optionally substituted with or fused with R$^6$;

each E is independently selected from the group consisting of Ht; —O—Ht; Ht—Ht; —O—R$^3$; —NR$^2$R$^3$; C$_1$–C$_6$ alkyl, which may be optionally substituted with one or more groups selected from the group consisting of R$^4$ and Ht; C$_2$–C$_6$ alkenyl, which may be optionally substituted with one or more groups selected from the group consisting of R$^4$ and Ht; and phenyl fused with 5–6 membered heterocycle;

each R$^4$ is independently selected from the group consisting of —OR$^2$, —C(O)—NHR$^2$, —S(O)$_2$—NHR$^2$, halo, —NR$^2$—C(O)—R$^2$ and —CN;

each R$^5$ is independently selected from the group consisting of H and C$_1$–C$_4$ alkyl optionally substituted with aryl; and each R$^6$ is independently selected from the group consisting of aryl, carbocycle and heterocycle, wherein said aryl, carbocycle or heterocycle may be optionally substituted with one or more groups selected from the group consisting of oxo, —OR$^5$, —R$^5$, —N(R$^5$)(R$^5$), —N(R$^5$)—C(O)—R$^5$, —OH, —CN, —CO$_2$R$^5$, —C(O)—N(R$^5$)(R$^5$), halo and —CF$_3$.

It is also an object of this invention to provide pharmaceutical compositions comprising the sulfonamides of formula I and methods for their use as inhibitors of HIV aspartyl protease.

DETAILED DESCRIPTION OF THE INVENTION

In order that the invention herein described may be more fully understood, the following detailed description is set forth. In the description, the following abbreviations are used:

| Designation | Reagent or Fragment |
|---|---|
| Ac | acetyl |
| Me | methyl |
| Et | ethyl |
| Bn | benzyl |
| Trityl | triphenylmethyl |

-continued

| Designation | Reagent or Fragment |
|---|---|
| Asn | D- or L-asparagine |
| Ile | D- or L-isoleucine |
| Phe | D- or L-phenylalanine |
| Val | D- or L-valine |
| Boc | tert-butoxycarbonyl |
| Cbz | benzyloxycarbonyl (carbobenzyloxy) |
| DCC | dicyclohexylcarbodiimide |
| DBU | 1,8-diazabicyclo[5.4.0]undec-7-ene |
| DIC | diisopropylcarbodiimide |
| DIEA | diisopropylethylamine |
| DMF | dimethylformamide |
| DMSO | dimethylsulfoxide |
| EDC | 1-(3-dimethylaminopropyl)-3-ethylcarbodiimide hydrochloride |
| EtOAc | ethyl acetate |
| Fmoc | 9-fluorenylmethoxycarbonyl |
| HOBt | 1-hydroxybenzotriazole |
| HQSU | 1-hydroxysuccinimide |
| iBu | iso-butyl |
| NCA | N-carboxyanhydride |
| t-Bu | tert-butyl |
| TFA | trifluoroacetic acid |
| THP | tetrahydropyran |
| THF | tetrahydrofuran |
| TMSCl | chlorotrimethylsilane |

The following terms are employed herein:

Unless expressly stated to the contrary, the terms "—SO$_2$—" and "—S(O)$_2$—" as used herein refer to a sulfone or sulfone derivative (i.e., both appended groups linked to the S), and not a sulfinate ester.

The term "backbone" refers to the structural representation of a compound of this invention, as set forth in the figures drawn in this application.

For the compounds of formula I, and intermediates thereof, the stereochemistry of the explicitly shown hydroxyl is defined relative to D on the adjacent carbon atom, when the molecule is drawn in an extended zig-zag representation (such as that drawn for compounds of formula VI). If both OH and D reside on the same side of the plane defined by the extended backbone of the compound, the stereochemistry of the hydroxyl will be referred to as "syn". If OH and D reside on opposite sides of that plane, the stereochemistry of the hydroxyl will be referred to as "anti".

As used herein, the term "alkyl", alone or in combination with any other term, refers to a straight-chain or branch-chain saturated aliphatic hydrocarbon radical containing the specified number of carbon atoms, or where no number is specified, preferably from 1–10 and more preferably from 1–5 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, preferably from 2–10 carbon atoms and more preferably, from 2–6 carbon atoms. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like.

The term "aryl", alone or in combination with any other term, refers to a carbocyclic aromatic radical (such as phenyl or naphthyl) containing the specified number of carbon atoms, preferably from 6–14 carbon atoms, and more preferably from 6–10 carbon atoms. Examples of aryl radicals include, but are not limited to phenyl, naphthyl, indenyl, indanyl, azulenyl, fluorenyl, anthracenyl and the like.

The term "cycloalkyl", alone or in combination with any other term, refers to a cyclic saturated hydrocarbon radical containing the specified number of carbon atoms, preferably from 3–7 carbon atoms. Examples of cycloalkyl radicals include, but are not limited to, cyclopropyl, cyclobutyl, cyclopentyl, cyclohexyl, cycloheptyl and the like.

The term "cycloalkenyl", alone or in combination with any other term, refers to a cyclic hydrocarbon radical containing the specified number of carbon atoms with at least one endocyclic carbon-carbon bond. Where no number of carbon atoms is specified, a cycloalkenyl radical preferably has from 5–7 carbon atoms. Examples of cycloalkenyl radicals include, but are not limited to, cyclopentenyl, cyclohexenyl, cyclopentadienyl and the like.

The term "THF" refers to a tetrahydrofuran ring attached at any ring carbon resulting in a stable structure.

The term "carbocycle" refers to a stable non-aromatic 3- to 8-membered carbon ring radical which may be saturated, mono-unsaturated or poly-unsaturated. The carbocycle may be attached at any endocyclic carbon atom which results in a stable structure. Preferred carbocycles have 5–6 carbons. Examples of carbocycle radicals include, but are not limited to, cyclopropyl, cyclobutyl, cyclopentyl, cyclohexyl, cycloheptyl, cyclopentenyl, cyclohexenyl, cyclopentadienyl and the like.

The term "heterocycle", unless otherwise defined herein, refers to a stable 3–7 membered monocyclic heterocyclic ring or 8–11 membered bicyclic heterocyclic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. In addition, any ring nitrogen may be optionally substituted with a substituent $R^2$, as defined herein for compounds of formula I. A heterocycle may be attached at any endocyclic carbon or heteroatom which results in the creation of a stable structure. A heterocycle may be attached at any endocyclic carbon or heteroatom which results in the creation of a stable structure. Preferred heterocycles include 5–7 membered monocyclic heterocycles and 8–10 membered bicyclic heterocycles. Preferred heterocycles defined above include, for example, benzimidazolyl, imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, oxazolyl, benzoxazolyl, oxopiperidinyl, oxopyrroldinyl, oxoazepinyl, azepinyl, isoxazolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, dioxanyl, dioxolanyl, tetrahydrofurotetrahydrofuranyl, tetrahydropyranotetrahydrofuranyl, tetrahydrofurodihydrofuranyl, tetrahydropyranodihydrofuranyl, dihydropyranyl, dihydrofuranyl, dihydrofurotetrahydrofuranyl, dihydropyranotetrahydrofuranyl, sulfolanyl and the like.

The term "halo" refers to a radical of fluorine, chlorine, bromine or iodine.

The term "linker" refers to a structural unit through which two other moieties are joined. For example, the term "$C_1$–$C_3$ alkyl linker" refers to a 1–3 carbon unit which attaches two other moieties together.

The term "oxygenated heterocycle", unless expressly modified to the contrary, refers to an aromatic or non-aromatic, preferably non-aromatic, 5–7 membered monocyclic or 8–11 membered bicyclic heterocycle containing 1–3, and more preferably 1–2, endocyclic oxygen heteroatoms and 0–2 endocyclic nitrogen or sulfur heteroatoms. Preferably, such oxygenated heterocycles contain only endocyclic oxygen heteroatoms. Examples of oxygenated heterocycles, include, but are not limited to: dioxanyl, dioxolanyl, tetrahydrofuranyl, tetrahydrofurotetrahydrofuranyl, tetrahydropyranyl, tetrahydropyranotetrahydrofuranyl, tetrahydrofurodihydrofuranyl, tetrahydropyranodihydrofuranyl, dihydropyranyl, dihydrofuranyl, dihydrofurotetrahydrofuranyl and dihydropyranotetrahydrofuranyl and the like.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "anti-viral agent" or "anti-retroviral agent" refers to a compound or drug which possesses viral inhibitory activity. Such agents include reverse transcriptase inhibitors (including nucleoside and non-nucleoside analogs) and protease inhibitors. Preferably the protease inhibitor is an HIV protease inhibitor. Examples of nucleoside analog reverse transcriptase inhibitors include, but are not limited to, zidovudine (AZT), dideoxycytidine (ddC), didanosine (ddI), stavudine (d4T), 3TC, 935U83, 1592U89 and 524W91. Examples of non-nucleoside analog reverse transcriptase inhibitors include, but are not limited to delavirdine (U90) and nevirapine. Examples of HIV protease inhibitors include, but are not limited to, saquinavir (Ro 31-8959), MK 639, ABT 538 (A80538), AG 1343, XM 412, XM 450, BMS 186318 and CPG 53,437.

The term "leaving group" or "LG" refers to groups readily displaceable by a nucleophile, such as an amine, alcohol, phosphorous or thiol nucleophile or their respective anions. Such leaving groups are well known and include carboxylates, N-hydroxysuccinimide, N-hydroxybenzotriazole, halogen (halides), triflates, tosylates, mesylates, alkoxy, thioalkoxy, phosphinates, phosphonates and the like. Other potential nucleophiles include organometallic reagents known to those skilled in the art. In addition, the term "leaving group" or "LG" is meant to encompass leaving group precursors (i.e., moieties that can be easily converted to a leaving group upon simple synthetic procedures such as alkylation, oxidation or protonation). Such leaving group precursors and methods for converting them to leaving groups are well known to those of ordinary skill in the art. Leaving group precursors include, for instance, secondary and tertiary amines. By way of example, the moiety —$N(R_3)(R_4)$, while not itself a leaving group, is encompassed by the term "leaving group" or "LG" because it can be readily converted to a leaving group such as —$N^+CH_3(R_3)(R_4)$.

The term "protecting group" refers to a suitable chemical group which may be attached to a functional group and removed at a later stage to reveal the intact functional group. Examples of suitable protecting groups for various functional groups are described in T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995).

The term "silyl" refers to a trisubstituted silicon radical in which the substituents are independently $C_1$–$C_8$ alkyl, $C_5$–$C_7$ aryl or $C_5$–$C_7$ carbocycle. Examples of silyl groups include, but are not limited to, trimethylsilyl, triethylsilyl, triisopropylsilyl, t-butyldimethylsilyl, t-butyldiisopropylsilyl, t-butyldiphenylsilyl, triphenylsilyl, cyclohexyldimethylsilyl and the like.

The term "pharmaceutically effective amount" refers to an amount effective in treating HIV infection in a patient either as monotherapy or in combination with other agents. The term "treating" as used herein refers to the alleviation of symptoms of a particular disorder in a patient or the improvement of an ascertainable measurement associated with a particular disorder. Specifically, with respect to HIV, effective treatment using the compounds and compositions of this invention would result in an improvement in an HIV associated ascertainable measurement. Such measurements include, but are not limited to, reduction in viral load in plasma or another defined tissue compartment as measured by, e.g. RT-PCR or branched-chain DNA PCR or culturable virus measurements, β-2 microglobulin or p24 levels, number of $CD_4^+$ cells or ratio of $CD_4^+$/$CD_8^+$ cells, or functional markers such as improvement in quality of life, ability to carry out normal functions, reduction of dementia, or immunosuppression-related effects including, but not limited to, opportunistic infections and tumors. The term "prophylactically effective amount" refers to an amount effective in preventing HIV infection in a patient. As used herein, the term "patient" refers to a mammal, including a human.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the antiretroviral agent.

The term "point of attachment" refers to the atom through which a moiety is attached to a specified structure. When a point of attachment may be optionally methylated, the point of attachment is the carbon atom through which a moiety is attached to a specified structure.

The term "substituted", whether express or implied and whether preceded by the term "optionally" or not, refers to the replacement of one or more hydrogen radicals in a given structure with the radical of a specified substituent. When more than one position in a given structure may be substituted with a substituent selected from a specified group, the substituents may be either the same or different at every position. Typically, when a structure may be optionally substituted, 0–3 substitutions are preferred, and 0–1 substitution is most preferred. Most preferred substituents are those which enhance protease inhibitory activity or intracellular antiviral activity in permissive mammalian cells or immortalized mammalian cell lines, or which enhance deliverability by enhancing solubility characteristics or enhancing pharmacokinetic or pharmacodynamic profiles as compared to the unsubstituted compound. Other most preferred substituents include those used in the compounds shown in Table I.

As used herein, the compounds of this invention, including the compounds of formula I, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the explicitly shown hydroxyl in formula (I) or to "E" in formula (I).

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, p-toluenesulfonic, tartaric, acetic, citric, methanesulfonic, ethanesulfonic, formic, benzoic, malonic, naphthalene-2-sulfonic and benzenesulfonic acids. Preferred acids include hydrochloric, sulfuric, methanesulfonic and ethanesulfonic acids. Methanesulfonic acid is most preferred. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and $N-(C_{1-4}$ alkyl$)_4^+$ salts.

The term "thiocarbamates" refers to compounds containing the functional group N—$SO_2$—O.

The compounds of this invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. The explicitly shown hydroxyl is also preferred to be syn to D, in the extended zig-zag conformation between the nitrogens shown in compounds of formula I.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

The compounds of the present invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate and undecanoate.

This invention also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chlorides, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The novel sulfonamides of this invention are those of formula I:

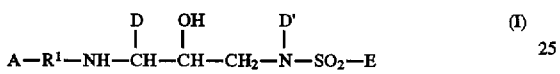

$$A-R^1-NH-CH(D)-CH(OH)-CH_2-N(D')-SO_2-E \quad (I)$$

wherein:

each $R^1$ is independently selected from the group consisting of —C(O)—, —S(O)$_2$—, —C(O)—C(O)—, —O—C(O)—, —O—S(O)$_2$, —NR$^2$—S(O)$_2$—, —NR$^2$—C(O)— and —NR$^2$—C(O)—C(O)—; preferably $R^1$ is —C(O)— or —O—C(O)—; and most preferably $R^1$ is —O—C(O)—;

each A is independently selected from the group consisting of 5-7 membered non-aromatic monocyclic oxygenated heterocycles containing from 1-3 endocyclic oxygens, which may be optionally benzofused, optionally attached through a $C_1$-$C_3$ alkyl linker, preferably not attached through a linker, and optionally fused with a 5-7 membered monocyclic heterocycle containing from 1-2 endocyclic heteroatoms, preferably not fused, and wherein tetrahydrofuran and tetrahydrofurotetrahydrofuran are expressly excluded; preferably A is selected from the group consisting of 5-6 membered non-aromatic monocyclic oxygenated heterocycles containing from 1-2 endocyclic oxygen atoms, which may be optionally attached through a $C_1$-$C_3$ alkyl linker and optionally fused with a 5-6 membered monocyclic oxygenated heterocycle; more preferably A is dioxanyl, dioxolanyl, dioxolanylmethyl, tetrahydrofurodihydrofuranyl, tetrahydropyranotetrahydrofuranyl or tetrahydropyranodihydrofuranyl; even more preferably A is 1,3-dioxanyl; and most preferably A is 1,3-dioxan-5-yl;

each Ht is independently selected from the group consisting of $C_3$-$C_7$ carbocycle; $C_6$-$C_{10}$ aryl; phenyl fused with heterocycle; and heterocycle; wherein any member of said Ht may be optionally substituted with one or more substituents selected from the group consisting of oxo, —OR$^2$, —R$^2$, —N(R$^2$)(R$^2$), —NHOH, —R$^2$—OH, —CN, —CO$_2$R$^2$, —C(O)—N (R$^2$)(R$^2$), —S(O)$_2$—N (R$^2$)(R$^2$), —N (R$^2$)—C(O)—R$^2$, —C(O)—R$^2$, —S(O)$_n$—R$^2$, —OCF$_3$, —S(O)$_n$—R$^6$, —N (R$^2$)—S(O)$_2$(R$^2$), halo, —CF$_3$, —NO$_2$, —R$^6$ and —O—R$^6$;

each $R^2$ is independently selected from the group consisting of H and $C_1$-$C_3$ alkyl optionally substituted with $R^6$;

each $R^3$ is independently selected from the group consisting of H, Ht, $C_1$-$C_6$ alkyl and $C_2$-$C_6$ alkenyl wherein any member of said $R^3$, except H, may be optionally substituted with one or more substituents selected from the group consisting of —OR$^2$, —C(O)—NH—R$^2$, —S(O)$_n$—N(R$^2$)(R$^2$), Ht, —CN, —SR$^2$, —CO$_2$R$^2$, NR$^2$—C(O)—R$^2$;

each n is independently 1 or 2;

each D and D' is independently selected from the group consisting of $R^6$; $C_1$-$C_5$ alkyl, which may be optionally substituted with one or more groups selected from —OR$^2$, —R$^3$, —S—R$^{6'}$—O—R$^6$ and $R^6$; $C_2$-$C_4$ alkenyl, which may be optionally substituted with one or more groups selected from the group consisting of —OR$^2$, —R$^3$, —O—R$^6$ and $R^6$; and $C_3$-$C_6$ carbocycle, which may be optionally substituted with or fused with $R^6$; preferably each D is $C_1$-$C_5$ alkyl, which may be optionally substituted with one or more Ht, more preferably D is $C_1$-$C_5$ alkyl, which may be optionally substituted with one group selected from $C_6$-$C_{10}$ aryl and $C_3$-$C_6$ carbocycle, even more preferably D is selected from the group consisting of benzyl, isobutyl, cyclopentylmethyl and cyclohexylmethyl and most preferably, D is benzyl or isobutyl; preferably each D' is selected from the group consisting of $C_1$-$C_5$ alkyl optionally substituted with $R^6$ (wherein each $R^6$ is independently selected from the group consisting of aryl, carbocycle and heterocycle, wherein said aryl, heterocycle or carbocycle may be optionally substituted with one or more groups selected from the group consisting of oxo, —OR$^5$, —R$^5$, —N(R$^5$)(R$^5$), —N(R$^5$)—C(O)—R$^5$, —R$^5$—OH, —CN, —CO$_2$R$^5$, —C(O)—N(R$^5$)(R$^5$), halo and —CF$_3$ and each $R^5$ is independently selected from the group consisting of H and $C_1$-$C_3$ alkyl), and more preferably D' is selected from the group consisting of $C_1$-$C_4$ alkyl optionally substituted with one 3-6 membered carbocycle or one 5-6 membered heterocycle, and most preferably, D' is selected from the group consisting of isobutyl, cyclopentylmethyl and cyclohexylmethyl;

each E is independently selected from the group consisting of Ht; —O—Ht; Ht—Ht; —O—R$^3$; —NR$^2$R$^3$; $C_1$-$C_6$ alkyl, which may be optionally substituted with one or more groups selected from the group consisting of $R^4$ and Ht; $C_2$-$C_6$ alkenyl, which may be optionally substituted with one or more groups selected from the group consisting of $R^4$ and Ht; and phenyl fused with heterocycle or carbocycle; preferably each E is Ht and more preferably, E is phenyl optionally substituted with one or more substituents selected from the group consisting of —OR$^2$, —R$^2$, —N(R$^2$)(R$^2$), —N(R$^2$)—C(O)—R$^2$, —R$^2$—OH, —CN, —CO$_2$R$^2$, —C(O)—N(R$^2$)(R$^2$), halo, and —CF$_3$; or phenyl fused with a 5-7 membered heterocycle or carbocycle; and even more preferably, E is phenyl substituted with one substituent selected from the group consisting of —OH, —OCH$_3$, —NH$_2$, —NHCOCH$_3$, —SCH$_3$, and —CH$_3$; or phenyl fused with 5-6 membered heterocycle, and most preferably, E is phenyl substituted with —NH$_2$ (preferably in the meta- or para-position);

each $R^4$ is independently selected from the group consisting of —OR$^2$, —C(O)—NHR$^2$, —S(O)$_2$—NHR$^2$, halo, —NR$^2$—C(O)—R$^2$ and —CN;

each $R^5$ is independently selected from the group consisting of H, $C_1$-$C_4$ alkyl optionally substituted with aryl; and each $R^6$ is independently selected from the group consisting of aryl, carbocycle and heterocycle, wherein said aryl, carbocycle or heterocycle may be optionally substituted with one or more groups selected from the group consisting of oxo, —$OR^5$, —$R^5$, —$N(R^5)(R^5)$, —$N(R^5)$—$C(O)$—$R^5$, —$R^5$—$OH$, —$CN$, —$CO_2R^5$, —$C(O)$—$N(R^5)(R^5)$, halo and —$CF_3$.

In an alternate embodiment of this invention, A is selected from the group consisting of 5–7 membered monocyclic heterocycles containing from 1–3 heteroatoms, which are methylated at the point of attachment and may be optionally benzofused, optionally attached through a $C_1$–$C_3$ alkyl linker and optionally fused with a 5–7 membered monocyclic heterocycle containing from 1–2 endocyclic heteroatoms; preferably A is selected from the group consisting of 5–6 membered non-aromatic monocyclic oxygenated heterocycles containing from 1–2 endocyclic oxygen atoms, which are methylated at the point of attachment and may be optionally attached through a $C_1$–$C_3$ alkyl linker and optionally fused with a 5–6 membered monocyclic oxygenated heterocycle; more preferably A is 3-methyltetrahydrofuranyl, 4-methyltetrahydrofurotetrahydrofuranyl, or 5-methyl-1,3-dioxanyl.

Except where expressly noted to the contrary, the term "[variable] as defined for formula I" refers to the definitions shown directly above.

Preferred compounds of formula I include those compounds having at least one variable defined as the preferred, more preferred, even more preferred or most preferred definition above. More preferred compounds of formula I include those compounds having at least two to three variables defined independently as the preferred, more preferred, even more preferred or most preferred definitions above. Most preferred compounds of formula I include those compounds having at least four to five variables independently defined as the preferred, more preferred, even more preferred or most preferred definitions above.

Table I illustrates preferred compounds of this invention:

TABLE I

TABLE I-continued

![structure: A-O-C(=O)-N(H)-CH(D)-CH(OH)-CH2-N(D')-SO2-E]

| COMPOUND | A | D | D' | E |
|---|---|---|---|---|
| 8 (Isomer B) | bicyclic tetrahydropyran-fused ether (+) or (−) | −CH₂−phenyl | −CH₂−cyclopentyl | 3-aminophenyl (NH₂) |
| 9 (Isomer A) | bicyclic tetrahydropyran-fused ether (+) or (−) | −CH₂−phenyl | −CH₂−CH(CH₃)₂ | 3-aminophenyl (NH₂) |
| 10 (Isomer B) | bicyclic tetrahydropyran-fused ether (+) or (−) | −CH₂−phenyl | −CH₂−CH(CH₃)₂ | 3-aminophenyl (NH₂) |
| 11 | bicyclic tetrahydropyran-fused ether (±) | −CH₂−phenyl | −CH₃ | 4-NHCOCH₃−phenyl |
| 12 | bicyclic tetrahydropyran-fused ether (±) | −CH₂−CH(CH₃)₂ | −CH₂−cyclohexyl | 3-aminophenyl (NH₂) |
| 13 | tetrahydropyran-4-yl | −CH₂−phenyl | −CH₂−cyclohexyl | 4-aminophenyl (NH₂) |
| 14 | tetrahydropyran-4-yl | −CH₂−phenyl | −CH₂−CH(CH₃)₂ | 4-aminophenyl (NH₂) |
| 15 | 3-methyltetrahydrofuran-3-yl | −CH₂−phenyl | −CH₂−cyclopentyl | 3-aminophenyl (NH₂) |

TABLE I-continued

| COMPOUND | A | D | D' | E |
|---|---|---|---|---|
| 16 | (tetrahydrofuranyl-CH₃ ether) | —CH₂—(phenyl) | —CH₂—CH(CH₃)CH₃ | (phenyl)-NH₂ |

More preferred compounds of this invention are selected from the group consisting of compounds 3; 4; 5 and 6 wherein each compound has the formula shown in Table I.

The sulfonamides of this invention may be synthesized using conventional techniques. Advantageously, these compounds are conveniently synthesized from readily available starting materials.

The compounds of this invention are among the most readily synthesized HIV protease inhibitors known. Previously described HIV protease inhibitors often contain four or more chiral centers, numerous peptide linkages and/or require air-sensitive reagents (such as organometallic complexes) to effect their synthesis. The relative ease with which the compounds of this invention can be synthesized represents an enormous advantage in the large scale production of these compounds.

In general, sulfonamides of formula I are conveniently obtained from β-amino acids and their formal derivatives having the general formula II:

$$(W)(Q)N—CH(D)—Y \quad (II)$$

wherein W is hydrogen or P; P is defined as an amino protecting group; Q is hydrogen, benzyl or A—R$^1$—; Y is —C(O)OH, —C(O)H, or —CH$_2$OH; and D and A—R$^1$— are as defined above for the compounds of formula I. W and Q may also be taken together with the nitrogen to which they are attached to form a heterocycle, an example of such a construction is phthalimide. Suitable amino protecting groups are described in numerous references, including T. W. Greene and P. G. M. Wuts, *Protective Groups in Organic Synthesis*, 2d Ed., John Wiley and Sons (1991); L. Fieser and M. Fieser, *Fieser and Fieser's Reagents for Organic Synthesis*, John Wiley and Sons (1994); and L. Paquette, ed. *Encyclopedia of Reagents for Organic Synthesis*, John Wiley and Sons (1995). Examples of such amino protecting groups include, but are not limited to, groups such as Boc, Cbz or Alloc, or alternatively, the amine may be protected as an alkyl derivative such as N,N-dibenzyl or trityl. Such α-amino acid derivatives are often commercially available or may be conveniently prepared from commercially available α-amino acid derivatives using known techniques. Although this invention envisions the use of racemic mixtures of such starting materials, a single enantiomer in the S configuration is preferred.

Using known techniques, the α-amino acid derivative of general formula P—N(Q)—CH(D)—COOH may be readily converted to an amino ketone derivative of general formula P—N(Q)—CH(D)—CO—CH$_2$—X, wherein P, Q and D are as defined for compounds of formula II and X is a leaving group which suitably activates the α-carbon (i.e., increases the susceptibility of the methylene to nucleophilic attack). Suitable leaving groups are well known in the art and include halides, dialkyl sulfonium salts and sulfonates, such as methanesulfonate, trifluoromethanesulfonate or 4-toluenesulfonate. X may also be a hydroxyl which is converted in situ to a leaving group (e.g. by treatment with a trialkyl- or triarylphosphine in the presence of a dialkylazodicarboxylate). Methods for the formation of such amino ketone derivatives also are well known to those of skill in the art (see, for example, S. J. Fittkau, *J. Prakt. Chem.*, 315, p. 1037 (1973)). Alternatively, certain amino ketone derivatives are commercially available (e.g., from Bachem Biosciences, Inc., Philadelphia, Pa.).

The amino ketone derivative may then be reduced to the corresponding amino alcohol, represented by the formula P—N(Q)—CH(D)—CH(OH)—CH$_2$—X, wherein P, Q and D are as defined for compounds of formula II and X is a leaving group. Alternatively, the amino ketone derivative can be reduced later in the synthetic scheme. Many techniques for reduction of amino ketone derivatives such as P—N(Q)—CH(D)—CO—CH$_2$—X are well known to those of ordinary skill in the art (G. J. Quallich and T. M. Woodall, *Tetrahedron Lett.*, 34, p. 785 (1993) and references cited therein; and Larock, R. C. "Comprehensive Organic Transformations", pp. 527–547, VCH Publishers, Inc.© 1989 and references cited therein). A preferred reducing agent is sodium borohydride. The reduction reaction is conducted at a temperature of from about −40° C. to about 40° C. (preferably, at about 0° C. to about 20° C.), in a suitable solvent system such as, for example, aqueous or neat tetrahydrofuran or a lower alcohol, such as methanol or ethanol. Although this invention envisions both stereospecific and non-stereospecific reduction of the amino ketone derivative P—N(Q)—CH(D)—CO—CH$_2$—X, stereoselective reduction is preferred. Stereoselective reduction may be accomplished by use of chiral reagents known in the art or by the use of an achiral reducing agent on a chiral substrate. In the present invention, stereoselective reduction may be conveniently achieved, for instance, under non-chelating reducing conditions, where chiral induction of the newly formed hydroxyl group is set by the stereochemistry of the D group (i.e., Felkin-Ahn addition of hydride). We particularly prefer stereoselective reductions wherein the resulting hydroxyl is syn to D. We have found that when the hydroxyl group is syn to D, the final sulfonamide product is an HIV protease inhibitor of higher potency than the anti diastereomer.

The hydroxyl group of the amino alcohol may optionally be protected by any known oxygen protecting group (such as trialkylsilyl, benzyl, acetal or alkyloxymethyl) to yield a protected amino alcohol having the formula P—N(Q)—CH (D)—C(OR⁷)—CH₂—X, wherein P, Q and D are as defined for compounds of formula II, X is a leaving group and R⁷ is H or any suitable hydroxy protecting group. Several useful protecting groups are described in T. W. Greene and P. G. M. Wuts, *Protective Groups in Organic Synthesis*, 2d Ed., John Wiley and Sons (1991); L. Fieser and M. Fieser, *Fieser and Fieser's Reagents for Organic Synthesis*, John Wiley and Sons (1994); and L. Paquette, ed. *Encyclopedia of Reagents for Organic Synthesis*, John Wiley and Sons (1995).

The amino alcohol may then be reacted with a nucleophilic amine compound to form an intermediate of formula III:

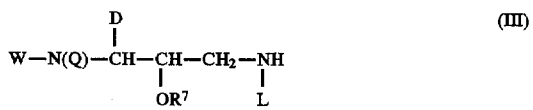

wherein W, Q and D are as defined in formula II, R⁷ is H or any suitable oxygen protecting group and L is either D' (as described for compounds of formula I) or hydrogen.

Alternatively, an amino acid derivative may be reacted with a nucleophilic nitro compound (e.g., a nitromethane anion or a derivative thereof) which can be reduced in one or more steps to yield an intermediate of formula III.

In a particularly advantageous synthetic scheme, simultaneous activation of the methylene and protection of the alcohol may be accomplished by forming an N-protected amino epoxide from the oxygen and its adjacent methylene to give an intermediate of formula IV:

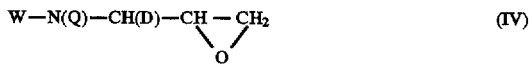

wherein W, Q and D are as defined above for compounds of formula II. Suitable solvent systems for preparing the N-protected amino epoxide include ethanol, methanol, isopropanol, tetrahydrofuran, dioxane, dimethylformamide and the like (including mixtures thereof). Suitable bases for producing the epoxide include alkali metal hydroxides, potassium t-butoxide, DBU and the like. A preferred base is potassium hydroxide.

Alternatively, the N-protected amino epoxide may be prepared by reacting an (alkylthio) or (phenylthio)acetic acid dianion with a cyclic N-carboxyanhydride of a protected α-amino acid (such as BOC-Phe-NCA, available from Propeptide). A preferred acetic acid dianion is (methylthio)acetic acid dianion. The resulting amino ketone may then be reduced (e.g., with sodium borohydride). The resulting amino alcohol is readily converted to the amino epoxide by quaternization (e.g., with methyl iodide) followed by ring closure (using, for example, sodium hydride).

Reaction of the N-protected amino epoxide (or other suitably activated intermediate) with an amine is carried out neat, i.e. in the absence of solvent, or in the presence of a polar solvent such as lower alkanols, water, dimethylformamide or dimethylsulfoxide. The reaction can be carried out conveniently between about −30° C. and 120° C., preferably between about −5° C. and 100° C. Alternatively, the reaction may be carried out in the presence of an activating agent, such as activated alumina in an inert solvent, preferably an ether, such as diethyl ether, tetrahydrofuran, dioxane, or tert-butyl methyl ether, conveniently from about room temperature to about 110° C., as described by Posner and Rogers, *J. Am Chem. Soc.*, 99, p. 8208 (1977). Other activating reagents include lower trialkyl-aluminum species, such as triethylaluminum, or dialkylaluminum halide species, such as diethylaluminum chloride (Overman and Flippin, *Tetrahedron Letters*, p. 195 (1981)). Reactions involving these species are conveniently carried out in inert solvents such as dichloromethane, 1,2-dichloroethane, toluene, or acetonitrile between about 0° C. and about 110° C. Further methods of displacing leaving groups, or opening epoxides with amines or their equivalents such as azides or trimethylsilyl cyanide (Gassman and Guggenheim, *J. Am. Chem. Soc.* 104, p. 5849 (1982)), are known and will be apparent to those of ordinary skill in the art.

Compounds of formulae II, III and IV, and functionality-protected derivatives thereof, are useful as intermediates for the preparation of compounds of formula I. In those cases where L represents D', compounds of formula III may be converted to compounds of formula I by reaction with sulfonyl-activated species to form sulfonamides, sulfonylureas, thiocarbamates and the like. Methods for preparing such sulfonyl-activated species are well within the ordinary skill of the art. Typically, sulfonyl halides are used to obtain sulfonamides. Many sulfonyl halides are commercially available; others may be easily obtained using conventional synthetic techniques (Gilbert, E. E. "Recent Developments in Preparative Sulfonation and Sulfation" Synthesis 1969: 3 (1969) and references cited therein; Hoffman, R. V. "M-Trifluoromethylbenzenesulfonyl Chloride" Org. Synth. Coll. Vol. VII, John Wiley and Sons (1990); Hartman, G. D. et. al. "4-Substituted Thiophene-and Furan-2-sulfonamides as Topical Carbonic Anhydrase Inhibitors" *J. Med. Chem.*, 35, p. 3822 (1992) and references cited therein. Sulfonyl ureas are usually obtained by the reaction of an amine with sulfuryl chloride or a suitable equivalent such as sulfuryl-bis-imidazole or sulfuryl-bis-N-methyl imidazole. Thiocarbamates are typically obtained by the reaction of an alcohol with sulfuryl chloride or a suitable equivalent such as sulfuryl-bis-imidazole or sulfuryl-bis-N-methyl imidazole.

In the case of compounds of formula III wherein L is hydrogen, conversion of the resultant primary amine to a secondary amine may be carried out by known techniques. Such techniques include reaction with an alkyl halide or alkyl sulfonate, or by reductive alkylation with an aldehyde or carboxylic acid or activated derivative thereof using, for instance, catalytic hydrogenation or sodium cyanoborohydride (Borch et al., *J. Am. Chem. Soc.*, 93, p. 2897 (1971)). Alternatively, the primary amine may be acylated followed by reduction with borane or another suitable reducing reagent, for example, as described by Cushman et al., *J. Org Chem.*, 56, p. 4161 (1991). This technique is especially useful in compounds of formula III where W represents a protecting group such as tert-butoxycarbonyl (Boc) or benzyloxycarbonyl (Cbz) and Q is H or where both W and Q are benzyl.

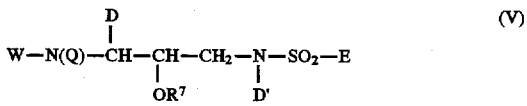

If variables W and Q of a particular compound of formula V represent removable protecting groups, removal of either or both groups followed by reaction of the resulting amine with an appropriate activated reagent will advantageously yield a different compound of formula V. For instance, reaction with an activated carboxylate, such as an acyl halide (e.g., acid fluorides, acid chlorides, and acid bromides), an activated ester such as 2- or 4-nitrophenyl esters, haloaryl esters (e.g., pentafluorophenyl or pentachlorophenyl), or 1-hydroxysuccinimide (HOSu) ester, a carbodiimide activated species, an anhydride, such as a symmetrical anhydride (e.g., isobutyl anhydride), or mixed carbonic-phosphoric or carbonic-phosphinic anhydrides, will yield the corresponding amide. Ureas may be obtained by reaction with isocyanates or amines in the presence of bis-activated carbonic acid derivatives such as phosgene or carbonyldiimdazole ("CDI"). Carbamates may be obtained by reaction with chlorocarbonates, with carbonates esterified with leaving groups such as 1-hydroxybenzotriazole ("HOBT"), MOSu, or 4-nitrophenol or with alcohols in the presence of bis-activated carbonic acid derivatives such as phosgene or its synthetic equivalents including diphosgene and triphosgene, or carbonyldiimdazole. Examples of such carbonates include, but are not limited to, 1,3-dioxan-5-yl-4-nitrophenyl carbonate, 3-methyltetrahydrofuran-3-yl-4-nitrophenyl carbonate, 4-nitrophenyl-tetrahydropyran-4-yl carbonate, 1,3-dioxolan-4-ylmethyl-4-nitrophenyl carbonate, 4-nitrophenyl-tetrahydrofurodihydrofuran-4-yl carbonate, and 4-nitrophenyl-tetrahydropyranodihydrofuran-4-yl carbonate and the like (see also: A. K. Ghosh, et al. *J. Med. Chem.* 37, p.2506 (1994)). 4-Nitrophenyl carbonates may be obtained by reaction of alcohols and 4-nitrophenyl chloroformates by methods known to those skilled in the art. In the reaction of 4-nitrophenyl chloroformate with glycerol formal to give 1,3-dioxan-5-yl-4-nitrophenyl carbonate and 1,3-dioxolan-4-ylmethyl-4-nitrophenyl carbonate, more of the dioxanyl product is produced relative to the dioxolanyl product if more basic conditions are utilized or if bis-4-nitrophenyl carbonate is used in place of the 4-nitrophenyl formate. While it is preferable to separate the 1,3-dioxan-5-yl-4-nitrophenyl carbonate and 1,3-dioxolan-4-ylmethyl-4-nitrophenyl carbonate products prior to further reaction with other amines, the mixture of the two carbonates can be reacted with a single amine and the two products separated at that stage. It will be readily recognized that in order to facilitate specific reactions, the protection of one or more potentially reactive groups followed by subsequent removal of that group may be required. Such modification to the reaction schemes outlined above are within the ordinary skill of the art.

A particularly useful synthetic scheme for producing preferred sulfonamide intermediates of formula VIII is shown below wherein for compounds of formulas VI, VII and VIII, W and Q are as defined above for compounds of formula II, D' and E are as defined for compounds of formula I, and P' is H or amino protecting groups:

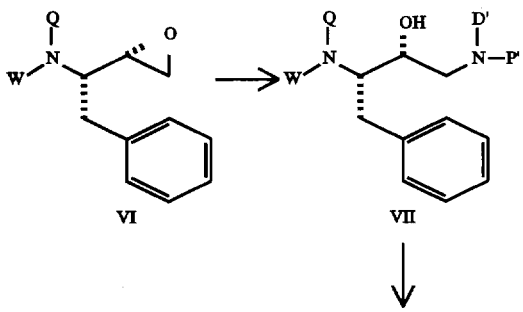

VI          VII

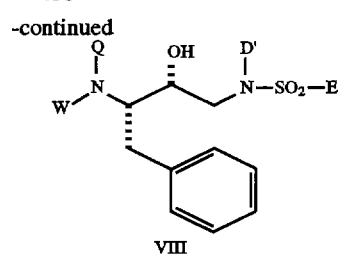

VIII

Compounds of formula VIII may be advantageously synthesized from readily available starting materials such as epoxide VI (see D. P. Getman, *J. Med. Chem.*, 36, p. 288 (1993) and B. E. Evans et al., *J. Org. Chem.*, 50, p. 4615 (1985)). Each step of the above synthetic scheme may be carried out as generally described above.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

The compounds of this invention may be modified by appending appropriate functionalites to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The novel compounds of the present invention are excellent ligands for aspartyl proteases, particularly HIV-1 and HIV-2 proteases. Accordingly, these compounds are capable of targeting and inhibiting late stage events in HIV replication, i.e., the processing of the viral polyproteins by HIV encoded proteases. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production of infectious virions, particularly from chronically infected cells. Compounds according to this invention advantageously inhibit the ability of the HIV-1 virus to infect immortalized human T cells over a period of days, as determined by an assay of extracellular p24 antigen—a specific marker of viral replication. Other antiviral assays have confirmed the potency of these compounds.

The compounds of this invention may be employed in a conventional manner for the treatment of viruses, such as HIV and HTLV, which depend on aspartyl proteases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally-infected patient in a pharmaceutically acceptable manner and in an amount effective to lessen the severity of the viral infection or to alleviate pathological effects associated with HIV infection or immunosuppression such as opportunistic infections or various cancers.

Alternatively, the compounds of this invention may be used in prophylactics and methods for protecting individuals against viral infection during a specific event, such as childbirth, or over an extended period of time. The compounds may be employed in such prophylactics either alone or together with other antiretroviral agents to enhance the efficacy of each agent. As such, the novel protease inhibitors of this invention can be administered as agents for treating or preventing HIV infection in a mammal.

The compounds of formula I, especially those having a molecular weight of less than about 700 g/mole, may be readily absorbed into the bloodstream of mammals upon oral administration. Compounds of formula I having a molecular weight of less than about 600 g/mole and aqueous solubility of greater than or equal to 0.1 mg/mL are most likely to demonstrate high and consistent oral availability. This surprisingly impressive oral availability makes such compounds excellent agents for orally-administered treatment and prevention regimens against HIV infection.

In addition to being orally bioavailable, the compounds of this invention also have an impressively high therapeutic index (which measures toxicity versus anti-viral effect). Accordingly, the compounds of this invention are effective at lower dosage levels than many previously described conventional antiretroviral agents and avoid many of the severe toxic effects associated with those drugs. The potential of these compounds to be delivered at doses far exceeding their effective antiviral levels is advantageous in slowing or preventing the possibility of resistant variants developing.

The compounds of this invention may be administered to a healthy or HIV-infected patient either as a single agent or in combination with other anti-viral agents which interfere with the replication cycle of HIV. By administering the compounds of this invention with other anti-viral agents which target different events in the viral life cycle, the therapeutic effect of these compounds is potentiated. For instance, the co-administered anti-viral agent can be one which targets early events in the life cycle of the virus, such as cell entry, reverse transcription and viral DNA integration into cellular DNA. Anti-HIV agents targeting such early life cycle events include, didanosine (ddI), dideoxycytidine (ddC), d4T, zidovudine (AZT), 3TC, 935U83, 1592U89, 524W91, polysulfated polysaccharides, sT4 (soluble CD4), ganiclovir, trisodium phosphonoformate, eflornithine, ribavirin, acyclovir, alpha interferon and trimetrexate. Additionally, non-nucleoside inhibitors of reverse transcriptase, such as TIBO, delavirdine (U90) or nevirapine, may be used to potentiate the effect of the compounds of this invention, as may viral uncoating inhibitors, inhibitors of trans-activating proteins such as tat or rev, or inhibitors of the viral integrase.

Combination therapies according to this invention exert an additive or synergistic effect in inhibiting HIV replication because each component agent of the combination acts on a different site of HIV replication. The use of such combination therapies may also advantageously reduce the dosage of a given conventional anti-retroviral agent which would be required for a desired therapeutic or prophylactic effect, as compared to when that agent is administered as a monotherapy. Such combinations may reduce or eliminate the side effects of conventional single anti-retroviral agent therapies, while not interfering with the anti-retroviral activity of those agents. These combinations reduce potential of resistance to single agent therapies, while minimizing any associated toxicity. These combinations may also increase the efficacy of the conventional agent without increasing the associated toxicity. In particular, we have discovered that in combination with other anti-HIV agents, the compounds of this invention act in an additive or synergistical manner in preventing the replication of HIV in human T cells. Preferred combination therapies include the administration of a compound of this invention with AZT, ddI, ddC, d4T, 3TC, 935U83, 1592U89, 524W91 or a combination thereof.

Alternatively, the compounds of this invention may also be co-administered with other HIV protease inhibitors such as saquinavir (Ro 31-8959, Roche), MK 639 (Merck), ABT 538 (A-80538, Abbott), AG 1343 (Agouron), XM 412 (DuPont Merck), XM 450 (DuPont Merck), BMS 186318 (Bristol-Meyers Squibb) and CPG 53,437 (Ciba Geigy) or prodrugs of these or related compounds to increase the effect of therapy or prophylaxis against various viral mutants or members of HIV quasi species.

We prefer administering the compounds of this invention as single agents or in combination with retroviral reverse transcriptase inhibitors, such as nucleoside derivatives, or other HIV aspartyl protease inhibitors, including multiple combinations comprising from 3–5 agents. We believe that the co-administration of the compounds of this invention with retroviral reverse transcriptase inhibitors or HIV aspartyl protease inhibitors may exert a substantial additive or synergistic effect, thereby preventing, substantially reducing, or completely eliminating viral replication or infection or both, and symptoms associated therewith. Additionally, as the viruses are capable of developing resistance to certain aspartyl protease inhibitors quite rapidly, we believe that administration of a combination of agents may aid in slowing the development of resistant viruses relative to single agents alone.

The compounds of this invention can also be administered in combination with immunomodulators and immunostimulators (e.g., bropirimine, anti-human alpha interferon antibody, IL-2, GM-CSF, interferon alpha, diethyldithiocarbamate, tumor necrosis factor, naltrexone, tuscarasol, and rEPO); and antibiotics (e.g., pentamidine isethiorate) to prevent or combat infection and disease associated with HIV infections, such as AIDS, ARC and HIV-associated cancers.

When the compounds of this invention are administered in combination therapies with other agents, they may be administered sequentially or concurrently to the patient. Alternatively, pharmaceutical compositions according to this invention may comprise a combination of an aspartyl protease inhibitor of this invention and one or more therapeutic or prophylactic agents.

Although this invention focuses on the use of the compounds disclosed herein for preventing and treating HIV infection, the compounds of this invention can also be used as inhibitory agents for other viruses which depend on similar aspartyl proteases for obligatory events in their life cycle. These viruses include other AIDS-like diseases caused by retroviruses, such as simian immunodeficiency viruses, HTLV-I and HTLV-II. In addition, the compounds of this invention may also be used to inhibit other aspartyl proteases, and in particular, other human aspartyl proteases, including renin and aspartyl proteases that process endothelin precursors.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as dα-tocopherol polyethyleneglycol 1000 succinate, or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$-, and $\gamma$-cyclodextrin, or chemically modified derivatives such as hydroxyalkylcyclodextrins, including 2- and 3-hydroxypropyl-$\beta$-cyclodextrins, or other solublized derivatives may also be advantageously used to enhance delivery of compounds of formula I.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the active ingredient compound are useful in the prevention and treatment of viral infection, including infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide or may be derivatized to bind to a stable resin as a tethered substrate for affinity chromatography applications. For example, a compound of formula I may be tethered to an affinity column to purify recombinantly produced HIV protease. Derivatization of the compounds of this invention to produce affinity chromatography resins and the methods used to purify proteases using such resins are well known and within the skill of the art. These and other uses which characterize commercial aspartyl protease inhibitors will be evident to those of ordinary skill in the art. (See: Rittenhouse, J. et al. *Biochem. Biophys. Res. Commun.* 171, p. 60 (1990) and Heimbach, J. C. et al. Ibid 164, p. 955 (1989)).

In order that this invention be more fully understood, the following examples are set forth. These examples are for the purpose of illustration only and are not to be construed as limiting the scope of the invention in any way.

GENERAL MATERIALS AND METHODS

All temperatures are recorded in degrees Celsius. Thin layer chromatography (TLC) was carried out using 0.25 mm thick E. Merck silica gel 60 $F_{254}$ plates and elution with the indicated solvent system. Detection of the compounds was carried out by treating the plate with an appropriate visualizing agent, such as 10% solution of phosphomolybdic acid in ethanol or a 0.1% solution of ninhydrin in ethanol, followed by heating, and/or by exposure to UV light or iodine vapors when appropriate. Thick layer silica gel chromatography was also carried out using E. Merck 60 $F_{254}$ plates ("prep plates") of 0.5, 1.0, or 2.0 mm thickness. Following development of the plate, the band of silica containing the desired compound was isolated and eluted with an appropriate solvent. Analytical HPLC was carried out using a Water's Delta Pak, 5 µM silica, C18 reversed-phase column, 3.9 mm ID×15 cm L with a flow rate of 1.5 mL/min using the following table:
Mobile phase:
A=0.1% $CF_3CO_2H$ in $H_2O$
B=0.1% $CF_3CO_2H$ in $CH_3CN$
Gradient:
T=0 min., A (95%), B (5%)
T=20 min., A (0%), B (100%)
T=22.5 min., A (0%), B (100%)
Preparative HPLC was also carried out using $C_{18}$ reversed-phase media. HPLC retention times were recorded in minutes. NMR spectral data was recorded using a Bruker AMX500, equipped with either a reverse or QNP probe, at 500 MHz, and was taken in the indicated solvent.

We have measured the inhibition constants of each compound against HIV-1 protease using the method described essentially by M. W. Pennington et al., *Peptides* 1990, Gimet, E. and D. Andrew, Eds., Escom; Leiden, Netherlands (1990).

Compounds of formula I were tested for their antiviral potency in several virological assays. In the first assay, the compounds were added as a solution in dimethylsulfoxide (DMSO) to a test cell culture of CCRM-CEM cells, a strain of $CD4^+$ human T-cell lymphoma cells, previously acutely infected with $HIV_{IIIb}$ using standard protocols (see Meek, T. D. et al., "Inhibition of HIV-1 protease in infected T-lymphocytes by synthetic peptide analogues", *Nature*, 343, p. 90 (1990). Preferred compounds are those which are able to inhibit 90% of viral infectivity at a concentration of 1 µM or less. More preferred compounds are those which are able to inhibit 90% of viral infectivity at a concentration of 100 nM or less.

The effect of the compounds on inhibiting the replication of the virus was measured by determining the HIV extracellular p24 antigen concentration using a commercial enzyme immunoassay (obtained from Coulter Corporation, Hialeah, Fla.).

Depending on the cell type and the desired readout, syncytia formation, reverse-transcriptase (RT) activity, or cytopathic effect as assayed by a dye uptake method may also be used as readouts of antiviral activity. See H. Mitsuya and S. Broder, "Inhibition of the in vitro infectivity and cytopathic effect of human T-lymphotropic virus type III/lymphoadenopathy-associated virus (HTLV-III/LAV) by 2',3'-dideoxynucleosides", *Proc. Natl. Acad. Sci. USA*, vol. 83, pp. 1911–1915 (1986). The effect of compounds of formula I on clinical isolates of other HIV-1 strains was determined by obtaining low-passaged virus from HIV-infected patients and assaying the effect of the inhibitors in preventing infection of the HIV virus in freshly prepared human peripheral blood mononuclear cells (PBMCs).

Insofar as compounds of formula I are able to inhibit the replication of the HIV virus in human T-cells and furthermore, may be delivered orally to mammals, they are of evident clinical utility for the treatment of HIV infection. These tests are predictive of the compounds ability to inhibit HIV protease in vivo.

EXPERIMENTAL SECTION

EXAMPLE 1

N-Cyclopentylmethyl-N-((2 syn, 3S)-2-hydroxy-4-phenyl-3-(1,3-dioxan-5-yl-oxycarbonylamino))butyl-4-methoxy-benzenesulfonamide (Compound 1).

A. Glycerol formal (1.2 mL, 10.0 mmol) and N-methylmorpholine (1.1 mL, 10.0 mmol) were added to a solution of 4-nitrophenylchloroformate (2.01 g, 10.0 mmol) in 20 mL of $CH_2Cl_2$ at 0° C. The mixture was stirred overnight at room temperature then was washed with 0.5N aq. HCl, water, and brine. The organic phase was dried over $MgSO_4$ and concentrated. Purification by silica gel column chromatography (hexanes:EtOAc, 4:1) gave 1,3-dioxan-5-yl-4-nitrophenyl carbonate (0.85 g) and 1,3-dioxolan-4-ylmethyl-4-nitrophenyl carbonate (0.68 g). $^1H$ NMR consistent with structure.

B. 1,3-Dioxan-5-yl-4-nitrophenyl carbonate (0.079 g, 0.26 mmol) was added to a solution of N-cyclopentylmethyl-N-((2 syn, 3S)-2-hydroxy-4-phenyl-3-amino)butyl-4-methoxy-benzenesulfonamide hydrochloride salt (0.093 g, 0.198 mmol) and DIEA (0.086 mL, 0.496 mmol) in 1 mL of THF. The mixture was stirred overnight at R.T. whereupon the solvent was removed in vacuo. Chromatography of this material (10% EtOAc/$CH_2Cl_2$) gave the title compound (0.119 g). $R_f$=0.77; $CH_2Cl_2$ EtOAC, 6:4. HPLC retention time=14.99 min. $^1H$ NMR consistent with structure.

EXAMPLE 2

4-Amino-N-cyclopentylmethyl-N-((2 syn, 3S)-2-hydroxy-4-phenyl-3-(1,3-dioxan-5-yl-oxycarbonylamino))butyl-benzenesulfonamide (Compound 3).

A. N-Cyclopentylmethyl-N-((2 syn, 3S)-2-hydroxy-4-phenyl-3-(1,3-dioxan-5-yl-oxycarbonylamino))butyl-4-nitrobenzenesulfonamide (0.123 g, 0.213 mmol) and a catalytic amount of 10% Pd/C in 5 mL of MeOH was stirred overnight under an atmosphere of hydrogen. The mixture was filtered and concentrated to give the crude product. Purification of this material by chromatography (20% EtOAc/CH$_2$Cl$_2$) gave the title compound (0.082 g). R$_f$=0.43; CH$_2$Cl$_2$/EtOAc, 6:4. HPLC retention time=14.09 min. $^1$H NMR consistent with structure.

EXAMPLE 3

4-Amino-N-((2 syn, 3S)-2-hydroxy-4-phenyl-3-1,3-dioxan-5-yl-oxycarbonylamino)butyl-N-isobutyl-benzenesulfonamide (Compound 4).

A. The procedure described in Example 2A was performed using N-((2 syn, 3S)-2-hydroxy-4-phenyl-3-1,3-dioxan-5-yl-oxycarbonylamino)butyl-N-isobutyl-4-nitrobenzenesulfonamide (0.128 g, 0.232 mmol) to give the title compound (0.048 g). R$_f$=0.38; CH$_2$Cl$_2$/EtOAc, 6:4. HPLC retention time=13.11 min. $^1$H NMR consistent with structure.

EXAMPLE 4

3-Amino-N-((2 syn, 3S)-2-hydroxy-4-phenyl-3-1,3-dioxan-5-yl-oxycarbonylamino)butyl-N-isobutyl-benzenesulfonamide (Compound 5).

A. The procedure described in Example 2A was performed using N-((2 syn, 3S)-2-hydroxy-4-phenyl-3-1,3-dioxan-5-yl-oxycarbonylamino)butyl-N-isobutyl-3-nitrobenzenesulfonamide (0.118 g, 0.213 mmol) to give the title compound (0.051). R$_f$=0.23; CH$_2$Cl$_2$/MeOH, 95:5. HPLC retention time=13.33 min. $^1$H NMR consistent with structure.

EXAMPLE 5

3-Amino-N-cyclopentylmethyl-N-((2 syn, 3S)-2-hydroxy-4-phenyl-3-(1,3-dioxan-5-yl-oxycarbonylamino))butyl-benzenesulfonamide (Compound 6).

A. The procedure described in Example 2A was performed using N-cyclopentylmethyl-N-((2 syn, 3S)-2-hydroxy-4-phenyl-3-(1,3-dioxan-5-yl-oxycarbonylamino))butyl-3-nitrobenzenesulfonamide (0.128 g, 0.221 mmol) to give the title compound (0.037 g). R$_f$=0.35; CH$_2$Cl$_2$/MeOH, 95:5. HPLC retention time=14.16 min. $^1$H NMR consistent with structure.

EXAMPLE 6

N-Cyclopentylmethyl-N-((2 syn, 3S)-2-hydroxy-4-phenyl-3-(1,3-dioxolan-4-yl-methoxycarbonylamino))butyl-4-methoxy-benzenesulfonamide (Compound 2).

A. 1,3-Dioxolan-4-ylmethyl-4-nitrophenyl carbonate (0.086 g, 0.28 mmol)(prepared in Example 1A) was added to a solution of N-cyclopentylmethyl-N-((2 syn, 3S)-2-hydroxy-4-phenyl-3-amino)butyl-4-methoxy-benzenesulfonamide hydrochloride salt (0.102 g, 0.217 mmol) and DIEA (0.087 mL, 0.544 mmol) in 1 mL of THF. The mixture was stirred overnight at R.T. whereupon the solvent was removed in vacuo. Chromatography of this material (40% EtOAc/CH$_2$Cl$_2$) gave the title compound (0.130 g). R$_f$=0.71; CH$_2$Cl$_2$/EtOAC, 6:4. HPLC retention time=16.02 min. $^1$H NMR consistent with structure.

EXAMPLE 7

3-Amino-N-cyclopentylmethyl-N-((2 syn, 3S)-2-hydroxy-4-phenyl-3-(3-methyltetrahydrofuran-3-yl)oxycarbonylamino)butyl-benzenesulfonamide (Compound 15).

A. Methyl magnesium iodide (3.0M in Et$_2$O, 20 mL) was added to a solution of tetrahydrofuran-3-one (1.6 g, 18.6 mmol) in 15 mL of Et$_2$O at 0° C. After stirring 4 h at 0° C. the mixture was quenched with sat. aq. NH$_4$Cl solution and extracted with Et$_2$O. The combined extracts were dried over MgSO$_4$ and concentrated under reduced pressure to give the crude material. Purification by chromatography (CH$_2$Cl$_2$ to 1% MeOH/CH$_2$Cl$_2$ to 2% MeOH/CH$_2$Cl$_2$) gave 3-hydroxy-3-methyltetrahydrofuran (0.290 g). $^1$H NMR consistent with structure.

B. To a solution of 4-nitrophenyl chloroformate (0.86 g, 4.27 mmol) in 10 mL of CH$_2$Cl$_2$ was added N-methyl morpholine (0.43 g, 4.25 mmol) and 3-hydroxy-3-methyltetrahydrofuran (0.290 g, 2.84 mmol) in 5 mL of CH$_2$Cl$_2$. The mixture was stirred overnight at R.T. The solution was concentrated under reduced pressure and the resulting material purified by chromatography (CH$_2$Cl$_2$ to 10% Et$_2$O/CH$_2$Cl$_2$) to give 3-methyltetrahydrofuran-3-yl-4-nitrophenyl carbonate (0.560 g). $^1$H NMR consistent with structure.

C. 3-Methyltetrahydrofuran-3-yl-4-nitrophenyl carbonate (0.100 g, 0.374 mmol) was added to a solution of N-cyclopentylmethyl-N-((2 syn, 3S)-2-hydroxy-4-phenyl-3-aminobutyl-3-nitrobenzenesulfonamide hydrochloride salt (0.200 g) and triethylamine in 5 mL of CH$_2$Cl$_2$. The mixture was stirred overnight at R.T. whereupon the solvent was removed in vacuo. Chromatography of this material (CH$_2$Cl$_2$ to 10% Et$_2$O/CH$_2$Cl$_2$ to 1% MeOH/CH$_2$Cl$_2$) gave the nitro sulfonamide (0.200 g). $^1$H NMR consistent with structure.

D. A solution of the nitro sulfonamide prepared in Example 7C (0.200 g, 0.347 mmol) and 10% Pd/C (50 mg) in 5 mL of EtOAc was stirred under an atmosphere of hydrogen for 2 h. The crude product was isolated by filtration of the mixture and concentration of the filtrate. Purification by chromatography (CH$_2$Cl$_2$ to 1% MeOH/CH$_2$Cl$_2$ to 3% MeOH/CH$_2$Cl$_2$) gave the title compound (0.141 g). R$_f$=0.35; CH$_2$Cl$_2$/MeOH, 8:2. R$_f$=0.63; CH$_2$Cl$_2$/MeOH/NH$_4$OH, 90:10:1. HPLC retention time=13.75 min. $^1$H NMR consistent with structure.

EXAMPLE 8

3-Amino-N-((2 syn, 3S)-2-hydroxy-4-phenyl-3-(3-methyltetrahydrofuran-3-yl)oxycarbonylamino)butyl-N-isobutyl-benzenesulfonamide (Compound 16).

A. The procedure described in Example 7C was performed using N-(2 syn, 3S)-2-hydroxy-4-phenyl-3-aminobutyl-N-isobutyl-3-nitro-benzenesulfonamide hydrochloride salt (0.190 g, 0.415 mmol) and 3-methyltetrahydrofuran-3-yl-4-nitrophenyl carbonate (0.100 g, 0.374 mmol) to give the nitro sulfonamide (0.160 g). $^1$H NMR consistent with structure.

B. The procedure described in Example 7D was performed using the nitro sulfonamide prepared in Example 8A (0.160 g, 0.291 mmol) and stirring overnight to give the title compound (0.095 g, 63%). R$_f$=0.33; CH$_2$Cl$_2$/EtOAc, 8:2. R$_f$=0.58; CH$_2$Cl$_2$/MeOH/NH$_4$OH, 90:10:1. HPLC retention time=12.93 min. $^1$H NMR consistent with structure.

EXAMPLE 9

3-Amino-N-cyclopentylmethyl-N-((2 syn, 3S)-2-hydroxy-4-phenyl-3-(S)-tetrahydropyrano-[2,3-b]tetrahydrofuran-4-yloxycarbonylamino)butyl-benzenesulfonamide (Compound 7) and 3-Amino-N-cyclopentylmethyl-N-((2 syn, 3S)-2-hydroxy-4-phenyl-3-(R)-tetrahydropyrano-[2,3- b]tetrahydrofuran-4-yloxycarbonylamino)butyl-benzenesulfonamide (Compound 8).

A. The procedure of Example 7C was performed using 4-nitrophenyl-tetrahydropyrano-[2,3-b]tetrahydrofuran-4-yl carbonate (0.230 g, 0.74 mmol) and N-cyclopentylmethyl-N-((2 syn, 3S)-2-hydroxy-4-phenyl-3-aminobutyl-3-nitro-benzenesulfonamide hydrochloride salt (0.360 g, 0.74 mmol) to give the nitro sulfonamide (0.390 g). $^1$H NMR consistent with structure.

B. The procedure described in Example 7D was performed using the nitro sulfonamide prepared in Example 9A (0.350 g, 0.567 mmol) and stirring overnight to give compound 7 (0.055 g, 16%) and compound 8 (0.029 g, 9%) and a mixed fraction of the two compounds (0.131 g, 39%). $^1$H NMR consistent with structures. For 8: $R_f$=0.21; $CH_2Cl_2$/EtOAc, 8:2. $R_f$=0.24; $CH_2Cl_2$/MeOH, 97:3. HPLC retention time=14.69 min.

EXAMPLE 10

3-Amino-N-((2 syn, 3S)-2-hydroxy-4-phenyl-3-(S)-tetrahydropyrano-[2,3-b]tetrahydrofuran-4-yloxycarbonylamino)butyl-N-isobutyl-benzenesulfonamide (Compound 9) and 3-Amino-N-((2 syn, 3S)-2-hydroxy-4-phenyl-3-(R)-tetrahydropyrano-[2,3-b]tetrahydrofuran-4-yloxycarbonylamino)butyl-N-isobutyl-benzenesulfonamide (Compound 10).

A. The procedure of Example 7C was performed using 4-nitrophenyl-tetrahydropyrano-[2,3-b]tetrahydrofuran-4-yl carbonate (0.250 g, 0.81 mmol) and N-(2 syn, 3S)-2-hydroxy-4-phenyl-3-aminobutyl-N-isobutyl-3-nitro-benzenesulfonamide hydrochloride salt (0.380 g, 0.80 mmol) to give the nitro sulfonamide (0.310 g). $^1$H NMR consistent with structure.

B. The procedure described in Example 7D was performed using the nitro sulfonamide prepared in Example 10A (0.310 g, 0.524 mmol) and stirring overnight to give compound 9 (0.034 g) and compound 10 (0.047 g). $^1$H NMR consistent with structures. For 9: $R_f$=0.29; $CH_2Cl_2$/EtOAc, 8:2. $R_f$=0.24; $CH_2Cl_2$/MeOH, 97:3. HPLC retention time= 13.58 min. For 10: $R_f$=0.25; $CH_2Cl_2$/EtOAc, 8:2. $R_f$=0.23; $CH_2Cl_2$/MeOH, 97:3. HPLC retention time=13.72 min.

EXAMPLE 11

4-Acetamido-N-((2 syn, 3S)-2-hydroxy-4-phenyl-3-tetrahydropyrano-[2,3-b]tetrahydrofuran-4-yloxycarbonylamino)butyl-N-methyl-benzenesulfonamide (Compound 11).

A. A solution of 4-acetamido-N-((2 syn, 3S)-3-N'-t-butoxycarbonylamino-2-hydroxy-4-phenyl)butyl-N-methyl-benzenesulfonamide (0.100 g, 0.203 mmol) and 10% HCl in EtOAc (20 mL) was stirred for 3 h. The reaction was complete as judged by TLC analysis. The solution was concentrated under reduced pressure to give 130 mg of crude amine-HCl salt which was taken up in 5 mL of $CH_2Cl_2$ for use in further reactions.

B. The procedure of Example 10A was performed using the amine-HCl salt prepared in Example 11A (2.5 mL of solution) to give the title compound (0.051 g). $R_f$=0.05; $CH_2Cl_2$/MeOH, 97:3. $R_f$=0.47; $CH_2Cl_2$/MeOH/$NH_4OH$, 90:10:1. HPLC retention time=12.2 and 12.54 min. $^1$H NMR consistent with structure.

EXAMPLE 12

3-Amino-N-cyclohexylmethyl-N-((2 syn, 3S)-2-hydroxy-4-phenyl-3-(S)-tetrahydropyrano-[2,3-b]tetrahydrofuran-4-yloxycarbonylamino)butyl-benzenesulfonamide (Compound 12).

A. 3-Nitrophenyl sulfonyl chloride (0.270 g, 1.22 mmol) and solid $NaHCO_3$ (0.140 g, 1.57 mmol) were added to a solution of N-(3(S)-benzyloxycarbonylamino-2-hydroxy-5-methylhexyl)-N-cyclohexylmethylamine (0.310 g, 0.823 mmol) in 10 mL of $CH_2Cl_2$ and 10 mL of sat. aq. $NaHCO_3$. After stirring overnight at R.T., the solution was diluted with $CH_2Cl_2$ (100 mL) and the organic layers separated, dried over $MgSO_4$, and concentrated under reduced pressure. The resulting crude material was purified by chromatography ($CH_2Cl_2$ to 1% MeOH/$CH_2Cl_2$) to give the Cbz-amine sulfonamide (0.340 g). $^1$H NMR consistent with structure.

B. TMSCl (1.5 mL, 11.8 mmol) was slowly added to a solution of the Cbz-amine sulfonamide prepared in Example 12A (0.340 g, 0.605 mmol) and NaI (0.400 g, 2.67 mmol) in $CH_3CN$. After stirring 8 h. at R.T., the organic phases were concentrated and the residue partitioned between EtOAc and water. The organic phases were separated, dried over $MgSO_4$ and concentrated. The resulting amine was taken up in 5 mL of $CH_2Cl_2$ for use in further reactions.

C. The procedure described in Example 10A was performed using the amine prepared in Example 12B (2.5 mL of solution) to give the nitro sulfonamide (0.120 g, 66%). $^1$H NMR consistent with structure.

D. The procedure described in Example 7D was performed using the nitro sulfonamide prepared in Example 12A (0.120 g, 0.201 mmol) and stirring overnight to give the title compound (0.029 $R_f$=0.25; $CH_2Cl_2$/MeOH, 97:3. $R_f$=0.32; $CH_2Cl_2$/EtOAc, 8:2. HPLC retention time=15.36 and 16.79 min. $^1$H NMR consistent with structure.

EXAMPLE 13

3-Amino-N-cyclopentylmethyl-N-((2 syn, 3S)-2-hydroxy-4-phenyl-3-tetrahydropyran-4-yloxycarbonylamino)butyl-benzenesulfonamide (Compound 13).

A. A solution of 4-hydroxytetrahydropyran (0.500 g, 49.3 mmol) in 5 mL of $CH_2Cl_2$ was added to a solution of 4-nitrophenylchloroformate (1.18 g, 5.9 mmol) and N-methyl morpholine (0.59 g, 5.83 mmol) in 10 mL of $CH_2Cl_2$. After stirring overnight at R.T., the mixture was concentrated under reduced pressure and the residue purified by chromatography ($CH_2Cl_2$ to 10% $Et_2O$/$CH_2Cl_2$) to give 4-nitrophenyl-tetrahydropyran-4-yl carbonate (1.28). $^1$HNMR consistent with structure.

B. 4-Nitrophenyl-tetrahydropyran-4-yl carbonate (0.100 g, 0.374 mmol) was added to a solution of N-cyclopentylmethyl-N-((2 syn, 3S)-2-hydroxy-4-phenyl-3-aminobutyl-3-nitro-benzenesulfonamide hydrochloride salt (0.200 g, 0.413 mmol) and triethylamine (1 mL, 7.17 mmol) in 5 mL of $CH_2Cl_2$. After stirring overnight at R.T., the mixture was concentrated under reduced pressure and the residue purified by chromatography ($CH_2Cl_2$ to 10% $Et_2O$/$CH_2Cl_2$ to 1% MeOH/$CH_2Cl_2$) to give the nitro sulfonamide (0.110 g). $^1$H NMR consistent with structure.

C. The procedure described in Example 7D was performed using the nitro sulfonamide prepared in Example 13B (0.110 g, 0.191 mmol) and stirring overnight to give the title compound (0.050 g, 48%). $R_f$=0.24; $CH_2Cl_2$/EtOAc, 8:2. $R_f$=0.66; $CH_2Cl_2$/MeOH/$NH_4OH$, 90:10:1. HPLC retention time=13.39 min. $^1$H NMR consistent with structure.

EXAMPLE 14

3-Amino-N-((2 syn, 3S)-2-hydroxy-4-phenyl-3-tetrahydropyran-4-yloxycarbonylamino)butyl-N-isobutyl-benzenesulfonamide (Compound 14).

A. The procedure described in Example 13B was performed using N-(2 syn, 3S)-2-hydroxy-4-phenyl-3-aminobutyl-N-isobutyl-3-nitro-benzenesulfonamide hydrochloride salt (0.190 g, 0.415 mmol) to give the nitro sulfonamide (0.140 g). $^1$H NMR consistent with structure.

B. The procedure described in Example 7D was performed using the nitro sulfonamide prepared in Example 14A (0.140 g, 0.254 mmol) and stirring overnight to give the title compound (0.090 R$_f$=0.24; CH$_2$Cl$_2$/EtOAc, 8:2. R$_f$=0.59; CH$_2$Cl$_2$/MeOH/NH$_4$OH, 90:10:1. HPLC retention time=12.55 min. $^1$H NMR consistent with structure.

EXAMPLE 15

We measured the inhibition constants of the compounds listed in Table II against HIV-1 protease using the above-cited method of Pennington et al.

We also measured the anti-viral potency of the compounds in CCRM-CEM cells by the above-cited method of Meek et al. These results are also shown in Table II. K$_i$ and IC$_{90}$ values are expressed in nM. The designation "ND" is used where a given compound was not tested.

TABLE II

| Compound No. | K$_i^{(nM)}$ | IC$_{90}^{(nM)}$ |
|---|---|---|
| 1 | <0.10 | 5 |
| 2 | 0.30 | ND |
| 3 | 0.10 | 4 |
| 4 | 0.30 | 12 |
| 5 | 0.15 | 7 |
| 6 | <0.10 | 5 |
| 7 | <0.10 | ND |
| 8 | <0.10 | ND |
| 9 | 0.10 | ND |
| 10 | <0.10 | ND |
| 11 | 160. | ND |
| 12 | 1.5 | ND |
| 15 | 0.40 | ND |
| 16 | 1.5 | ND |

As demonstrated in Table II, all of the compounds tested displayed substantial inhibitory and anti-viral activity. Moreover, several of these compounds exhibited activity levels among the highest levels known to date for HIV protease inhibitors.

While we have described a number of embodiments of this invention, it is apparent that our basic constructions may be altered to provide other embodiments which utilize the products and methods of this invention. Therefore, it will be appreciated that the scope of this invention is to be defined by the appended claims, rather than by the specific embodiments which have been presented by way of example.

We claim:

1. A compound of formula I:

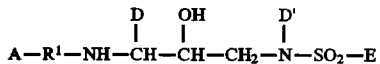

(I)

wherein:

each R$^1$ is independently selected from the group consisting of —C(O)—, —S(O)$_2$—, —C(O)—C(O)—, —O—C(O)—, —O—S(O)$_2$, —NR$^2$—S(O)$_2$—, —NR$^2$—C(O)— and —NR$^2$—C(O)—C(O)—;

each A is a 6 membered non-aromatic monocyclic oxygenated heterocycle containing 2 endocyclic oxygens, optionally attached through a C$_1$–C$_3$ alkyl linker;

each Ht is independently selected from the group consisting of C$_3$–C$_7$ carbocycle; and C$_6$–C$_{10}$ aryl; wherein any member of said Ht is optionally substituted with one or more substituents selected from the group consisting of oxo, —OR$^2$, —R$^2$, —N(R$^2$)(R$^2$), —NHOH, —R$^2$—OH, —CN, —CO$_2$R$^2$, —C(O)—N(R$^2$)(R$^2$), —S(O)$_2$—N(R$^2$)(R$^2$), —N(R$^2$)—C(O)—R$^2$, —C(O) —R$^2$, —S(O)$_n$—R$^2$, —OCF$_3$, —S(O)$_n$—R$^6$, —N(R$^2$) —S(O)$_2$(R$^2$), halo, —CF$_3$, —NO$_2$, —R$^6$, —S—CH$_3$ and —O—R$^6$;

each R$^2$ is independently selected from the group consisting of H and C$_1$–C$_3$ alkyl optionally substituted with R$^6$;

each R$^3$ is independently selected from the group consisting of H, Ht, C$_1$–C$_6$ alkyl and C$_2$–C$_6$ alkenyl wherein any member of said R$^3$, except H, is optionally substituted with one or more substituents selected from the group consisting of —OR$^2$, —C(O)—NH—R$^2$, —S(O)$_n$—N(R$^2$)(R$^2$), Ht, —CN, —SR$^2$, —CO$_2$R$^2$, and NR$^2$—C(O)—R$^2$;

each n is independently 1 or 2;

each D and D' is independently selected from the group consisting of R$^6$; C$_1$–C$_5$ alkyl, which is optionally substituted with one or more groups selected from —OR$^2$, —R$^3$, —S—R$^6$, —O—R$^6$ and R$^6$; C$_2$–C$_4$ alkenyl, which is optionally substituted with one or more groups selected from the group consisting of —OR$^2$, —R$^3$, —O—R$^6$ and R$^6$; and C$_3$–C$_6$ carbocycle, which is optionally substituted with or fused with R$^6$;

each E is independently selected from the group consisting of Ht; —O—Ht; Ht—Ht; —O—R$^3$; —NR$^2$R$^3$; C$_1$–C$_6$ alkyl, which is optionally substituted with one or more groups selected from the group consisting of R$^4$ and Ht; C$_2$–C$_6$ alkenyl, which is optionally substituted with one or more groups selected from the group consisting of R$^4$ and Ht; and phenyl fused with a 5–7 membered carbocycle;

each R$^4$ is independently selected from the group consisting of —OR$^2$, —C(O)—NHR$^2$, —S(O)$_2$—NHR$^2$, halo, —NR$^2$—C(O)—R$^2$ and —CN;

each R$^5$ is independently selected from the group consisting of H and C$_1$–C$_4$ alkyl optionally substituted with aryl; and each R$^6$ is independently selected from the group consisting of aryl, and carbocycle, each optionally substituted with one or more groups selected from the group consisting of oxo, —OR$^5$, —R$^5$, —N(R$^5$)(R$^5$), —N(R$^5$)—C(O)—R$^5$, —R$^5$—OH, —CN, —CO$_2$R$^5$, —C(O)—N(R$^5$)(R$^5$), halo and —CF$_3$.

2. The compound according to claim 1, wherein A is dioxanyl.

3. The compound according to claim 2, wherein A is 1,3-dioxanyl.

4. The compound according to claim 3, wherein A is 1,3-dioxan-5-yl.

5. A compound of formula I:

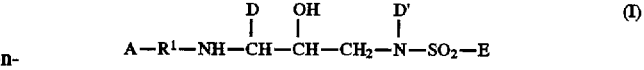

(I)

wherein:

each R$^1$ is independently selected from the group consisting of —C(O)—, —S(O)$_2$—, —C(O)—C(O)—, —O—C(O)—, —O—S(O)$_2$, —NR$^2$—S(O)$_2$—, —NR$^2$—C(O)— and —NR$^2$—C(O)—C(O)—;

each A is independently selected from the group consisting of a 6 membered monocyclic heterocycle, containing 2 endocyclic oxygens, which is methylated at the point of attachment and optionally attached through a $C_1$–$C_3$ alkyl linker;

each Ht is independently selected from the group consisting of $C_3$–$C_7$ carbocycle; and $C_6$–$C_{10}$ aryl; wherein any member of said Ht is optionally substituted with one or more substituents selected from the group consisting of oxo, —$OR^2$, $R^2$, —$N(R^2)(R^2)$, —NHOH, —$R^2$—OH, —CN, —$CO_2R^2$, —C(O)—$N(R^2)(R^2)$, —$S(O)_2$—$N(R^2)(R^2)$, —$N(R^2)$—C(O)—$R^2$, —C(O)—$R^2$, —$S(O)_n$—$R^2$, —$OCF_3$, —$S(O)_n$—$R^6$, —$N(R^2)$—$S(O)_2(R^2)$, halo, —$CF_3$, —$NO_2$, —$R^6$, —S—$CH_3$ and —O—$R^6$;

each $R^2$ is independently selected from the group consisting of H and $C_1$–$C_3$ alkyl optionally substituted with $R^6$;

each $R^3$ is independently selected from the group consisting of H, Ht, $C_1$–$C_6$ alkyl and $C_2$–$C_6$ alkenyl wherein any member of said $R^3$, except H, is optionally substituted with one or more substituents selected from the group consisting of —$OR^2$, —C(O)—NH—$R^2$, —$S(O)_n$—$N(R^2)(R^2)$, Ht, —CN, —$SR^2$, —$CO_2R^2$, and $NR^2$—C(O)—$R^2$;

each n is independently 1 or 2;

each D and D' is independently selected from the group consisting of $R^6$; $C_1$–$C_5$ alkyl, which is optionally substituted with one or more groups selected from —$OR^2$, —$R^3$, —S—$R^6$, —O—$R^6$ and $R^6$; $C_2$–$C_4$ alkenyl, which is optionally substituted with one or more groups selected from the group consisting of —$OR^2$, —$R^3$, —O—$R^6$ and $R^6$; and $C_3$–$C_6$ carbocycle, which is optionally substituted with or fused with $R^6$;

each E is independently selected from the group consisting of Ht; —O—Ht; Ht—Ht; —O—$R^3$; —$NR^2R^3$; $C_1$–$C_6$ alkyl, which is optionally substituted with one or more groups selected from the group consisting of $R^4$ and Ht; $C_2$–$C_6$ alkenyl, which is optionally substituted with one or more groups selected from the group consisting of $R^4$ and Ht; and phenyl fused with a 5–7 membered carbocycle;

each $R^4$ is independently selected from the group consisting of —$OR^2$, —C(O)—$NHR^2$, —$S(O)_2$—$NHR^2$, halo, —$NR^2$—C(O)—$R^2$ and —CN;

each $R^5$ is independently selected from the group consisting of H and $C_1$–$C_4$ alkyl optionally substituted with aryl; and each $R^6$ is independently selected from the group consisting of aryl, and carbocycle, each optionally substituted with one or more groups selected from the group consisting of oxo, —$OR^5$, —$R^5$, —$N(R^5)(R^5)$, —$N(R^5)$—C(O)—$R^5$, —$R^5$—OH, —CN, —$CO_2R^5$, —C(O)—$N(R^5)(R^5)$, halo and —$CF_3$.

6. The compound according to claim 5, wherein A is 5-methyl-1,3-dioxanyl.

7. The compound according to claims 1 or 5, wherein $R^1$ is —O—C(O)— or —C(O)—.

8. The compound according to claim 7, wherein $R^1$ is —O—C(O)—.

9. The compound according to claims 1 or 5, wherein D is methyl substituted with a substituent selected from the group $C_2$–$C_5$ alkyl, $C_3$–$C_7$ carbocycle and phenyl, which is optionally substituted with —O—$R^5$ or —S-phenyl.

10. The compound according to claim 9, wherein D is selected from the group consisting of benzyl, isobutyl and cyclohexylmethyl.

11. The compound according to claims 1 or 5, wherein:

each D' is selected from the group consisting of $C_1$–$C_6$ alkyl optionally substituted with $R^6$;

each $R^6$ is independently selected from the group consisting of aryl, and 3–6 membered carbocycle, each optionally substituted with one or more groups selected from the group consisting of oxo, —$OR^5$, —$R^5$, —$N(R^5)(R^5)$, —$N(R^5)$—C(O)—$R^5$, —$R^5$—OH, —CN, —$CO_2R^5$, —C(O)—$N(R^5)(R^5)$, halo and —$CF_3$; and each $R^5$ is independently selected from the group consisting of H and $C_1$–$C_3$ alkyl.

12. The compound according to claim 11, wherein D' is selected from the group consisting of isobutyl, cyclopentylmethyl and cyclohexylmethyl.

13. The compound according to claims 1 or 5, wherein:

each E is independently phenyl optionally substituted with one or more substituents selected from the group consisting of —$OR^2$, —$R^2$, —$N(R^2)(R^2)$, —$N(R^2)$—C(O)—$R^2$, —$R^2$—OH, —CN, —$CO_2R^2$, —C(O)—$N(R^2)(R^2)$, halo, —S—$CH_3$ and —$CF_3$; or phenyl fused with a 5–7 membered carbocycle;

each $R^2$ is independently selected from the group consisting of H and $C_1$–$C_3$ alkyl optionally substituted with $R^6$;

each $R^6$ is independently selected from the group consisting of aryl, and 3–6 membered carbocycle each optionally substituted with one or more groups selected from the group consisting of oxo, —$OR^5$, —$R^5$, —$N(R^5)(R^5)$, —$N(R^5)$—C(O)—$R^5$, —$R^5$—OH, —CN, —$CO_2R^5$, —C(O)—$N(R^5)(R^5)$, halo and —$CF_3$; and each $R^5$ is independently selected from the group consisting of H and $C_1$–$C_3$ alkyl.

14. The compound according to claim 13, $$\left[ A-R^1-NH-\overset{D}{\underset{|}{CH}}-\overset{OH}{\underset{|}{CH}}-CH_2-\overset{D'}{\underset{|}{N}}-SO_2-E \right]$$

wherein,

E is phenyl substituted with one or more substituents selected from the group consisting of —OH, —$OCH_3$, —$NH_2$, —$NHCOCH_3$, —S—$CH_3$, and —$CH_3$; or phenyl fused with a 5–6 membered carbocycle.

15. The compound according to claim 14, wherein E is phenyl substituted with —$NH_2$ at the meta- or para-position.

16. A compound selected from the group consisting of:

N-Cyclopentylmethyl-N-((2 syn, 3S)-2-hydroxy-4-phenyl-3-(1,3-dioxan-5-yl-oxycarbonylamino))butyl-4-methoxy-benzenesulfonamide;

4-Amino-N-cyclopentylmethyl-N-((2 syn, 3S)-2-hydroxy-4-phenyl-3-(1,3-dioxan-5-yl-oxycarbonylamino))butyl-benzenesulfonamide;

4-Amino-N-((2 syn, 3S)-2-hydroxy-4-phenyl-3-1,3-dioxan-5-yl-oxycarbonylamino)butyl-N-isobutyl-benzenesulfonamide;

3-Amino-N-((2 syn, 3S)-2-hydroxy-4-phenyl-3-1,3-dioxan-5-yl-oxycarbonylamino)butyl-N-isobutyl-benzenesulfonamide; and 3-Amino-N-cyclopentylmethyl-N-((2 syn, 3S)-2-hydroxy-4-phenyl-3-(1,3-dioxan-5-yl-oxycarbonylamino))butyl-benzenesulfonamide.

17. The compound according to claim 16 selected from the group consisting of:

4-Amino-N-cyclopentylmethyl-N-((2 syn, 3S)-2-hydroxy-4-phenyl-3-(1,3-dioxan-5-yl-oxycarbonylamino))butyl-benzenesulfonamide;

4-Amino-N-((2 syn, 3S)-2-hydroxy-4-phenyl-3-1,3-dioxan-5-yl-oxycarbonylamino)butyl-N-isobutyl-benzenesulfonamide;

3-Amino-N-((2 syn, 3S)-2-hydroxy-4-phenyl-3-1,3-dioxan-5-yl-oxycarbonylamino)butyl-N-isobutyl-benzenesulfonamide; and 3-Amino-N-cyclopentylmethyl-N-((2 syn, 3S)-2-hydroxy-4-phenyl-3-(1,3-dioxan-5-yl-oxycarbonylamino))butyl-benzenesulfonamide.

18. A pharmaceutical composition comprising a pharmaceutically effective amount of a compound according to claims 1, 5 or 14 and a pharmaceutically acceptable carrier, adjuvant or vehicle.

19. The pharmaceutical composition according to claim 18, wherein said pharmaceutical composition is orally administrable.

20. The pharmaceutical composition according to claim 18, further comprising one or more additional agents selected from the group consisting of other anti-viral agents and immunostimulators.

21. The pharmaceutical composition according to claim 20, wherein said other anti-viral agent or agents are protease inhibitors or reverse transcriptase inhibitors.

22. The pharmaceutical composition according to claim 21, wherein said protease inhibitor or inhibitors are HIV protease inhibitors.

23. The pharmaceutical composition according to claim 22, wherein said HIV protease inhibitor or inhibitors are selected from the group consisting of saquinavir (Ro 31-8959), MK 639, ABT 538 (A80538), AG 1343, XM 412, XM 450 and BMS 186318.

24. The pharmaceutical composition according to claim 21, wherein said reverse transcriptase inhibitor or inhibitors are nucleoside analogs.

25. The pharmaceutical composition according to claim 24, wherein said nucleoside analog or analogs are selected from the group consisting of zidovudine (AZT), dideoxycytidine (ddC), didanosine (ddI), stavudine (d4T), 3TC, 935U83, 1592U89 and 524W91.

26. The pharmaceutical composition according to claim 21, wherein said reverse transcriptase inhibitor or inhibitors are non-nucleoside analogs.

27. The pharmaceutical composition according to claim 26, wherein said non-nucleoside reverse transcriptase inhibitor or inhibitors are delavirdine (U90) or nevirapine.

28. A method for treating HIV infection in a mammal comprising the step of administering to said mammal a pharmaceutically effective amount of a pharmaceutical composition according to either claim 18.

29. A method for treating HIV infection in a mammal comprising the step of administering to said mammal a pharmaceutically effective amount of a pharmaceutical composition according to claim 20.

30. The method according to claim 28, further comprising the step of concurrently or sequentially administering to the mammal one or more additional agents selected from the group consisting of other anti-viral agents and immunostimulators.

31. The method according to claim 30, wherein said other anti-viral agent or agents are protease inhibitors or reverse transcriptase inhibitors.

32. The method according to claim 31, wherein said protease inhibitor or inhibitors are HIV protease inhibitors.

33. The method according to claim 32, wherein said HIV protease inhibitor or inhibitors are selected from the group consisting of saquinavir (Ro 31-8959), MK 639, ABT 538 (A80538), AG 1343, XM 412, XM 450, and BMS 186318.

34. The method according to claim 31, wherein said reverse transcriptase inhibitor or inhibitors are nucleoside analogs.

35. The method according to claim 34, wherein said nucleoside analog or analogs are selected from the group consisting of zidovudine (AZT), dideoxycytidine (ddC), didanosine (ddI), stavudine (d4T), 3TC, 935U83, 1592U89 and 524W91.

36. The method according to claim 31, wherein said reverse transcriptase inhibitor or inhibitors are non-nucleoside analogs.

37. The method according to claim 36, wherein said non-nucleoside reverse transcriptase inhibitor or inhibitors are delavirdine (U90) or nevirapine.

38. A method for treating HIV infection in a mammal comprising the step of administering to said mammal a pharmaceutically effective amount of a pharmaceutical composition according to claim 19.

39. The method according claim 38, further comprising the step of concurrently or sequentially administering to the mammal one or more additional agents selected from the group consisting of other anti-vital agents and immunostimulators.

40. The method according to claim 39, wherein said other anti-viral agents are protease inhibitors or reverse transcriptase inhibitors.

41. The method according to claim 40, wherein said protease inhibitors are HIV protease inhibitors.

42. The method according to claim 41, wherein said HIV protease inhibitor is selected from the group consisting of saquinavir (Ro 31-8959), MK 639, ABT 538 (A80538), AG 1343, XM 412, XM 450, and BMS 186318.

43. The method according to claim 40, wherein said reverse transcriptase inhibitors are nucleoside analogs.

44. The method according to claim 43, wherein said nucleoside analog is selected from the group consisting of zidovudine (AZT), dideoxycytidine (ddC), didanosine (ddI), stavudine (d4T), 3TC, 935U83, 1592U89 and 524W91.

45. The method according to claim 40, wherein said reverse transcriptase inhibitors are non-nucleoside analogs.

46. The method according to claim 45, wherein said non-nucleoside reverse transcriptase inhibitor is delavirdine (U90) or nevirapine.

* * * * *